United States Patent
Acedo et al.

(10) Patent No.: US 12,069,977 B2
(45) Date of Patent: Aug. 27, 2024

(54) METHODS AND SYSTEMS FOR PREDICTING CROP FEATURES AND EVALUATING INPUTS AND PRACTICES

(71) Applicant: Biome Makers Inc., West Sacramento, CA (US)

(72) Inventors: Alberto Acedo, Castile and León (ES); Nabeel Imam, Santiago (CL); Daniel Almonacid, Lafayette, CA (US); Adrian Ferrero, La Bañeza (ES)

(73) Assignee: Biome Makers Inc., Davis, CA (US)

( * ) Notice: Subject to any disclaimer, the term of this patent is extended or adjusted under 35 U.S.C. 154(b) by 322 days.

(21) Appl. No.: 17/587,046

(22) Filed: Jan. 28, 2022

(65) Prior Publication Data

US 2022/0240432 A1   Aug. 4, 2022

Related U.S. Application Data

(60) Provisional application No. 63/143,159, filed on Jan. 29, 2021, provisional application No. 63/143,534,
(Continued)

(51) Int. Cl.
*A01B 79/00* (2006.01)
*A01B 69/04* (2006.01)
(Continued)

(52) U.S. Cl.
CPC .......... *A01B 79/005* (2013.01); *A01B 69/008* (2013.01); *A01B 79/02* (2013.01);
(Continued)

(58) Field of Classification Search
CPC ...... G06Q 50/02; A01C 21/00; A01C 21/002; A01C 21/007; A01B 79/02; A01B 79/005;
(Continued)

(56) References Cited

U.S. PATENT DOCUMENTS 9,771,795 B2  9/2017  Knight et al.
10,395,355 B2  8/2019  Cohen
(Continued)

FOREIGN PATENT DOCUMENTS

WO   2020188114 A1   9/2020

OTHER PUBLICATIONS

Ali et al., "Hiseq Base Molecular Characterization of Soil Microbial Community, Diversity Structure, and Predictive Functional Profiling in Continuous Cucumber Planted Soil Affected by Diverse Cropping Systems in an Intensive Greenhouse Region of Northern China", May 28, 2019 (Year: 2019).*
(Continued)

*Primary Examiner* — John H Le

(57) ABSTRACT

A method and system for evaluating and predicting a set of crop-associated features at an agriculture site, the method comprising: receiving a set of samples associated with the agriculture site; generating a sample dataset upon processing the set of samples with a set of sample processing operations; generating a set of microbiome-associated features upon performing a set of transformation operations upon the sample dataset; and returning an analysis characterizing the set of crop-associated features based upon the set of microbiome-associated features. The method can further include steps for executing an action for producing a desired outcome in relation to the agriculture site, with respect to a specific soil type and a specific crop, based upon the analysis.

20 Claims, 19 Drawing Sheets

Related U.S. Application Data filed on Jan. 29, 2021, provisional application No. 63/143,600, filed on Jan. 29, 2021.

(51) Int. Cl.
| | | |
|---|---|---|
| *A01B 79/02* | (2006.01) | |
| *A01C 21/00* | (2006.01) | |
| *G06Q 50/02* | (2024.01) | |
| *G16B 20/20* | (2019.01) | |
| *G16B 20/40* | (2019.01) | |
| *G16B 40/00* | (2019.01) | |
| *G16B 40/30* | (2019.01) | |

(52) U.S. Cl.
CPC .......... *A01C 21/002* (2013.01); *A01C 21/007* (2013.01); *G06Q 50/02* (2013.01); *G16B 20/20* (2019.02); *G16B 20/40* (2019.02); *G16B 40/00* (2019.02); *G16B 40/30* (2019.02)

(58) Field of Classification Search
CPC ...... A01B 69/008; G16B 20/00; G16B 20/20; G16B 20/40; G16B 40/00; G16B 40/30
USPC ........................................................... 702/2
See application file for complete search history.

(56) References Cited

U.S. PATENT DOCUMENTS

| | | |
|---|---|---|
| 11,028,449 B2 | 6/2021 | Knight et al. |
| 2002/0103688 A1 | 8/2002 | Schneider |
| 2005/0234691 A1 | 10/2005 | Singh et al. |
| 2011/0137456 A1 | 6/2011 | Koselka et al. |
| 2012/0109614 A1 | 5/2012 | Lindores |
| 2014/0109249 A1 | 4/2014 | Turner et al. |
| 2014/0120063 A1 | 5/2014 | Sonnenburg |
| 2016/0217230 A1 | 7/2016 | Mewes et al. |
| 2016/0290918 A1 | 10/2016 | Xu et al. |
| 2018/0363031 A1 | 12/2018 | Becares et al. |
| 2020/0194126 A1 | 6/2020 | Lim et al. |
| 2020/0199556 A1 | 6/2020 | Hsu et al. |
| 2021/0009483 A1 | 1/2021 | Temme et al. |

OTHER PUBLICATIONS

International Search Report for PCT/US22/14202, mailed May 3, 2022.
Schmidt et al. "Agricultural management and plant selection interactively affect rhizosphere microbial community structure and nitrogen cycling", Microbiome vol. 7, Article No. 146, Jul. 11, 2019. Retrieved on Jul. 2, 2021. USA.
Girvan et al. "Community structure in social and biological networks", PNAS vol. 99, issue 12, Jun. 11, 2002. USA.
Van Klompenburg et al. "Crop yield prediction using machine learning: A systematic literature review", Computers and Electronics in Agriculture. 177(2020)105709, Aug. 18, 2020.
Konopka, Allan. "What is microbial community ecology", The ISME Journal. (2009) 3, 1223-1230. Aug. 6, 2009.
Netz et al. "Estimating computational limits on theoretical descriptions of biological cells", PNAS vol. 118, issue 6, Jan. 25, 2021. USA.
Veech, Joseph A. "A probablistic model for analysing species co-occurrence", Global Ecology and Biogeography, 2012.
Watts, et al. "Collective dynamics of 'small-world' networks". Nature vol. 393. Jun. 4, 1998.
Zele et al. "Ecology and evolution of facilitation among symbionts". Nature Communications (2018)9:4869.

\* cited by examiner

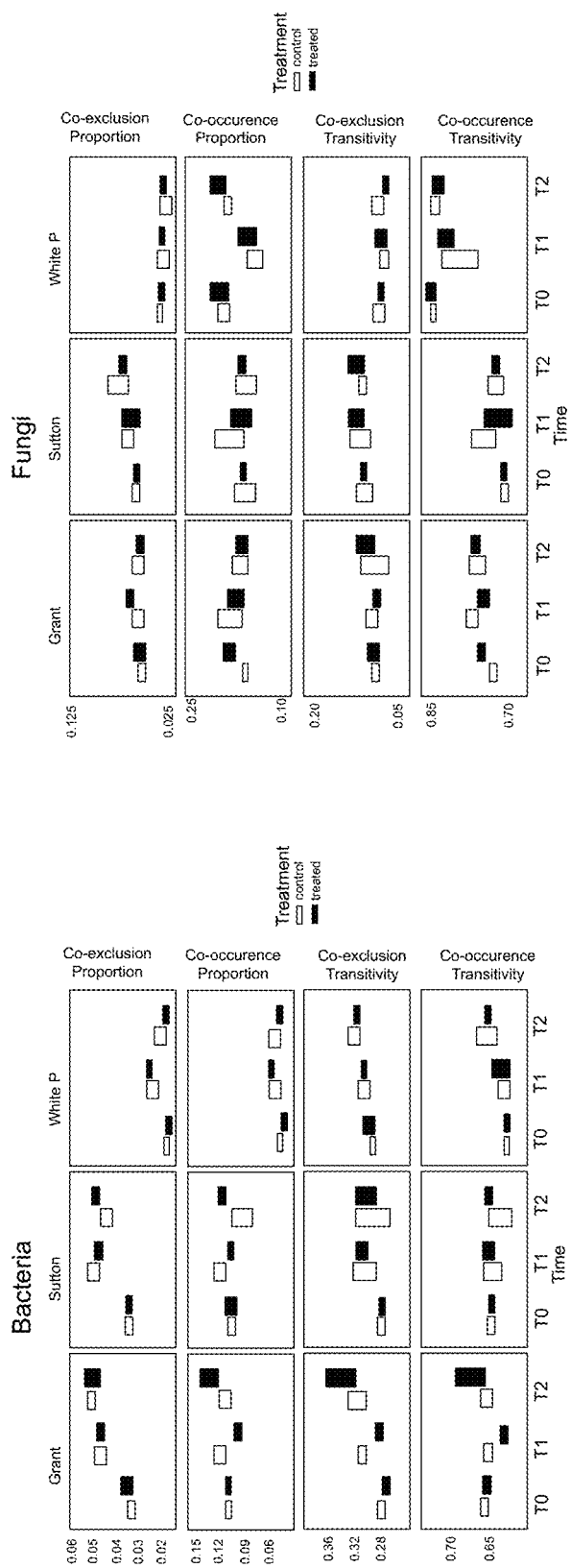
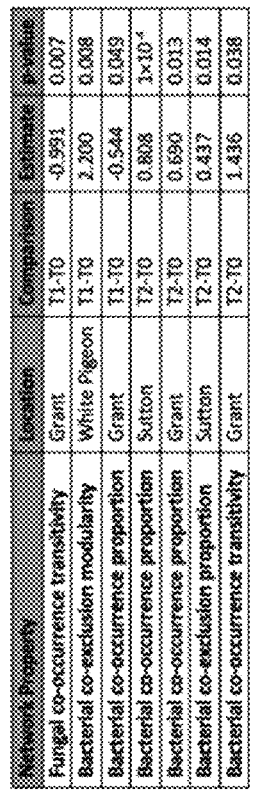
FIGURE 7A
FIGURE 7B
FIGURE 7C

METHODS AND SYSTEMS FOR PREDICTING CROP FEATURES AND EVALUATING INPUTS AND PRACTICES

CROSS-REFERENCE TO RELATED APPLICATIONS

This application claims the benefit of U.S. Provisional Application No. 63/143,159 filed on 29 Jan. 2021, U.S. Provisional Application No. 63/143,534 filed on 29 Jan. 2021, and U.S. Provisional Application No. 63/143,600 filed on 29 Jan. 2021, which are each incorporated in its entirety herein by this reference.

FIELD OF THE INVENTION

The disclosure generally relates to tools and systems implementing methods for sampling and characterizing agricultural sites.

BACKGROUND

Agriculture ecosystems are human-managed ecosystems subject to various ecological rules, in relation to steady state scenarios and in response to various perturbations. Understanding the ecological mechanisms behind soil microbial communities is a fruitful way to improve management practices, test various products, agricultural practices and/or other agricultural inputs, evaluate sustainability, and therefore improve agriculture site productivity. Acquisition and processing of the appropriate data from agriculture-associated samples, development of models for characterization of ecosystem statuses, and generation of outputs and implementation of actions for maintaining such ecosystems, improving yields, improving crop nutrient content, improving soil carbon sequestration characteristics, and/or improving produce shelf-life in a sustainable manner are all areas of innovation in which the inventions described herein provide value.

BRIEF DESCRIPTION OF THE FIGURES

FIGS. 7A-7C depict outputs of a method for evaluating and predicting crop features.

DETAILED DESCRIPTION OF THE INVENTION(S)

Figure 1:
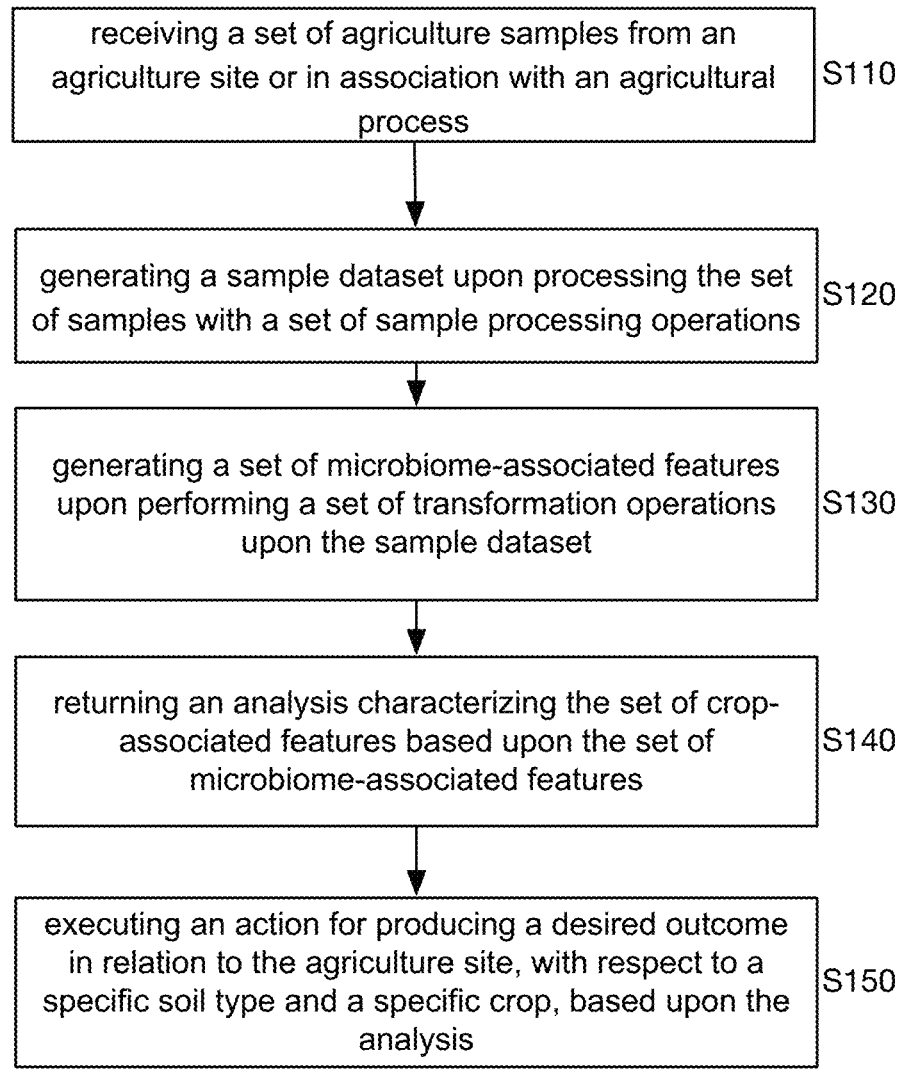
FIG. 1 depicts an embodiment of a workflow of a method for evaluating and predicting crop features.

The following description of the preferred embodiments of the invention is not intended to limit the invention to these preferred embodiments, but rather to enable any person skilled in the art to make and use this invention.

1. Benefits

The invention(s) described can confer several benefits over conventional systems, methods, and compositions.

The invention(s) provide systems and methods for prediction of various agriculture site and crop features, which are useful in downstream applications in relation to recommending or implementing various agriculture inputs and/or management practices to improve productivity or maintain health of the agriculture site.

Additionally, in embodiments, the invention(s) described implement rapid processing of samples and analysis of data generated from sample processing, in order to extract insights related to predicted features of crops and agriculture sites (e.g., yield, nutritional composition, etc.), in a manner that cannot be practically performed by the human mind.

Additionally, in embodiments, the invention(s) provide methods for determining microbiome-associated or -derived properties and functions, and/or properties and functions derived from network properties in local microbial, fungal, and/or other organism communities, and to use them to assess the impact of different agricultural inputs and/or practices (e.g., farming practices).

Additionally, in embodiments, The invention(s) can further provide methods and systems for evaluating, guiding, and/or executing implementation of various agricultural inputs and/or management practices for enhancement of yield (e.g., in relation to specific soil types and/or for specific crops) and/or improvement of agriculture site characteristics (e.g., with respect to health, with respect to sustainability).

In variations, the invention(s) described returned outputs for evaluating the effectiveness and potential mechanism of action of biostimulants with respect to different soil profiles and specific crops to generate precise product recommendations and implementation of interventions based on local conditions, for increasing crop yield. In a specific example, the invention(s) processed bulk soil and rhizosphere soil samples to determine microbial composition and structure, for evaluation of the effect of a *Bacillus amyloliquefaciens* strain QST713 inoculant on potato crops, with applications in improving crop yield. With application, the QST713 inoculant applied as a treatment according to the method was found to have a significant effect on yield through modulation of the structure of fungal and bacterial communities (e.g., measured using co-occurrence and co-exclusion networks), without causing a detectable long-lasting effect on the alpha- and beta-diversity patterns after harvest.

In embodiments, the method(s) promote agro-ecosystem sustainability through assessment of soil organism communities. In particular, the complexity of microbial communities, at both taxonomic and functional levels, is impossible to assess practically without systems and methods described herein, where the methods cannot be practically implemented by the human mind. The invention(s) thus process samples to extract patterns connecting sample microbiome composition with ecosystem function in order to drive interventions based upon the impact of biotic (e.g., interspecies interactions, intraspecies interactions) and abiotic (e.g. climate or anthropogenic disturbances) factors. As such, the invention(s) provide a new methodological framework—inferring emergent properties from local networks—with assessment and guidance of different ecological strategies in agricultural site communities. In practical applications, the methods can be used to restore soil functionality, predict yields, manage crop vulnerabilities, optimize their farming practices, and improve the sustainability of agricultural sites. Additionally or alternatively, the inventions can guide or inform management practices in relation to effects on soil carbon sequestration.

Additionally, the inventions described provide systems and a platform including architecture for agriculture sample extraction and processing, which provide improved tools for monitoring, forecasting, and responding to events (e.g., changes in productivity, events associated with management practices, environmental perturbations, product-induced perturbations, etc.) associated with one or more agricultural sites. Additionally or alternatively, the inventions can assess implementation of a plant variety and/or a seed variety at an agriculture site.

Additionally, the inventions apply outputs of the analyses to effect one or more actions (e.g., treatments) to maintain or improve the natural ecological site conditions, thereby providing practical applications of the method(s) and models involved.

Additionally, the inventions involve collection of samples from various agricultural sites, processing of samples to extract data features, application of one or more transformations to the data features to generate modified digital objects, create improved training data sets for machine learning/classification algorithms, and iteratively train the machine learning/classification algorithms, such that agriculture site statuses can be returned upon processing subsequent samples hitherto unseen by the algorithm.

In applications, the inventions can contribute to significantly increased yields of major/important crops (e.g., rice, wheat, soybeans, maize, potatoes, etc.) to improve global food production in relation to anticipated world population increases. Taking into account the effects of human intervention on soil ecology, the inventions can provide recommendations (management, treatment, etc.) that increase yield preserving ecology. In particular, using potato crops as an example, applications of the inventions can characterize yield (e.g., maximum potential yield) of potato crops based on current inputs and management practices, and/or recommend or implement agricultural inputs and improved practices for enhancement of yield and/or agriculture site characteristics.

Additionally or alternatively, the invention(s) can confer any other suitable benefit in any crop.

1.1 Definitions

The terms microbiome, microbiome information, microbiome data, microbiome population, microbiome panel and similar terms are used in the broadest possible sense, unless expressly stated otherwise, and would include: a census of currently present microorganisms, both living and nonliving, which may have been present months, years, millennia or longer; a census of components of the microbiome other than bacteria and archaea (e.g., viruses, microbial eukaryotes, etc.); population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

As used herein, the terms real-time microbiome data or information includes microbiome information that is collected or obtained at a particular setting or stage of an agricultural process for one or more agricultural sites.

As used herein, the terms derived microbiome information and derived microbiome data are to be given their broadest possible meaning, unless specified otherwise, and includes any real-time, microbiome information that has been computationally linked or used to create a relationship.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition in the industrial setting, or allows interpretation of a current or past occurrence.

Real time, derived, and predicted data can be collected and stored, and thus, become historic data for ongoing or future decision-making for a process, setting, or application.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

The term "microbiome", as used herein, refers to the ecological community of commensal, symbiotic, or pathogenic microorganisms in a sample.

The term "genome" as used herein, refers to the entirety of an organism's hereditary information that is encoded in its primary DNA sequence. The genome includes both the genes and the non-coding sequences. For example, the genome may represent a microbial genome or a mammalian genome.

Reference to "DNA region" should be understood as a reference to a specific section of genomic DNA. These DNA regions are specified either by reference to a gene name or a set of chromosomal coordinates. Both the gene names and the chromosomal coordinates would be well known to, and understood by, the person of skill in the art. In general, a gene can be routinely identified by reference to its name, via which both its sequences and chromosomal location can be routinely obtained, or by reference to its chromosomal coordinates, via which both the gene name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present applications, achieve the same outcome despite the fact that minor genetic variations between the actual nucleic acid sequences may exist between different bacterial strains. The present invention should therefore be understood to extend to all forms of DNA which arise from any other mutation, polymorphic or allelic variation.

Genetic sequences and/or fragments thereof can be targets of interest. Targets can additionally or alternatively include other nucleic acids (e.g., DNAs, RNAs), amino acids, proteins, other molecules, chemicals, other analytes, or other suitable material.

The term "sequencing" as used herein refers to sequencing methods for determining the order of the nucleotide bases—adenine, guanine, cytosine, and thymine—in a nucleic acid molecule (e.g., a DNA or RNA nucleic acid molecule).

The term "barcode" as used herein, refers to any unique, non-naturally occurring, nucleic acid sequence that may be used to identify the originating source of a nucleic acid fragment.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

2. Methods

As shown in FIG. 1, an embodiment of a method 100 for evaluating and predicting a set of crop-associated features at an agriculture site includes: receiving a set of samples from an agriculture site or in association with an agricultural process S110 (e.g., associated with an agricultural process at the agriculture site); generating a sample dataset upon processing the set of samples with a set of sample processing operations S120; generating a set of microbiome-associated features upon performing a set of transformation operations upon the sample dataset S130; and returning an analysis characterizing the set of crop-associated features based upon the set of microbiome-associated features S140.

In some variations, the method 100 can additionally or alternatively include executing an action for producing a desired outcome in relation to the agriculture site, with respect to a specific soil type and a specific crop, based upon the analysis S150.

The method 100 functions to generate predictions of crop-associated features at one or more agricultural sites, based upon a finite number of input features derived from processing of samples at the agriculture site(s). As such, the method 100 can generate insights for improvement of outcomes at the agriculture site(s), using novel processes, that provide improved efficiency and efficacy of achieving results at the agriculture site(s). Variations of the methods described can be implemented for various crop types, soil types, agriculture site locations, and/or other factors.

Furthermore, in downstream applications, refinement of models, system architecture, and sample processing techniques can be used to guide testing of, recommendation of, and/or implementation of (e.g., using automated or manual systems/devices) agricultural inputs, products for use, and management practices, in order to improve desired outcomes (e.g., in relation to yield, in relation to agriculture site health, in relation to sustainability, etc.). As such, the method (s) can provide steps for monitoring, controlling, and analyzing agriculture activities, with practical applications in food production, viticulture, bio-fuel production, and other agricultural activities.

In one example use-case, the method provided steps for and implemented systems that produced a greater percentage of potential yield (e.g., where actual yield typically corresponds to about 10-75% of the yield using standard methods). As such, the methods implement new technology for recovering a significant portion of lost yield.

Beyond characterizing ecological communities in terms of community aggregated traits (CATs), which result from the aggregation of taxa characteristics, the methods described provide characterizations and guidance for interventions based upon emergent properties (EPs) arising from specific taxa combinations and/or other features. In particular, the invention(s) produce models with architecture for contextualization of emergent properties into ecological mechanisms, with functionality for returning predictions of how communities would behave under various circumstances. Additionally, translating the idiosyncratic community behaviors into a measurable metric enables microbiome monitoring applications, such as in sustainable farming, food production, or human health. The methods thus discover, identify, and implement new biomarkers of agriculture site health and provide tools to provide accessibility of such information and guidance to suitable entities.

The method(s) described can be implemented by systems and platforms described in Section 3 below. Additionally or alternatively, the method(s) described can be implemented by embodiments, variations, and examples of systems described in U.S. application Ser. No. 15/779,531 filed on 5 Dec. 2016, which is herein incorporated in its entirety by this reference.

2.1 Methods—Sample Reception

Step S110 recites: receiving a set of agriculture samples from one or more agriculture sites or in association with an agricultural process, which functions to provide source material for generation of data from which models for characterizing statuses of the agriculture site(s) and/or various perturbations in downstream steps.

In step S110, samples can be received from various portions of the agriculture site(s) and/or states of processing of crops or other products derived from the agriculture site.

In embodiments, samples can be extracted from soil, another substrate, water used in agriculture, from various portions of crops, from organisms interacting with crops (e.g., parasites, other symbiotic organisms, etc.), from consumable products (e.g., food, beverages, supplements, etc.) derived from crops, from other surfaces (e.g., conduits used to deliver water or nutrients to crops, etc.), and/or from other suitable sampling sites. The samples can include solid samples (e.g., soil, sediment, rock, food samples). The samples can additionally or alternatively include liquid samples (e.g., surface water, sub-surface water, other liquids derived from crops, consumable products derived from crops, crop-derived products at various stages of processing or fermentation, etc.). The samples can additionally or alternatively include gas samples (e.g., samples from gases obtained from a greenhouse, gases produced during processing of crops or crop-derived products, etc.). Samples can be taken from crop portions (e.g., reproductive portions, petals, leaves, fruits, roots, trunks, flowers, pollen, etc.) and/or from crops in various states of health (e.g., healthy states, distressed states, diseased states, etc.).

Sample volumes can range from 0.01 grams to 1 kilogram (or greater than 1 kilogram, less than 0.01 gram). Additionally or alternatively, sample volumes can range from 1 microliter to 1 liter (or greater than 1 liter, less than 1 microliter).

Samples from different portions of the agriculture site, different portions of a crop, different portions or stages of a product being produces, and/or different sources can be combined in Step S110.

In examples, whole plants were collected and processed to extract samples from bulk soil (e.g., with vigorous shaking to acquire bulk soil from roots) and rhizospheres (e.g., by chopping roots separated from mother tubers), where, in more detail, a total of 185 samples (e.g., from treated and untreated plots at multiple agriculture sites) were collected over four time points at multiple locations associated with various metacommunities (e.g., in Michigan and Idaho), from planting (T0) to harvest (T3), focusing on the early changes occurring after one (T1) and two (T2) months from planting, where T0 and T3 were bulk soil samples, and T1 and T2 were rhizosphere soil samples. However, in alternative variations samples can be taken from other suitable sources associated with crops, agriculture sites, and/or product processing sites.

In relation to step S110, sample reception/collection can be performed using equipment (e.g., machinery, robotic apparatus configured to traverse an agricultural site in coordination with retrieval of the set of agriculture samples, other apparatus) and/or manually. In variations, sample reception/collection performed in Step S110 can use any one or more of: an instrument (e.g., scoop for soil, sharp instrument for extracting a portion of a crop specimen, etc.), a permeable substrate (e.g., a swab, a sponge, etc.), a nonpermeable substrate (e.g., tape, etc.), a container (e.g., vial, tube, bag, etc.) configured to receive a sample from the agriculture site or associated crops, and any other suitable sample-reception element. In a specific example, samples can be collected from one or more of: soil, other crop-associated solids, water, other crop-associated liquids, gases, and a crop component (e.g., root, stem, leaf, flower, seed, other plant component, etc.). In relation to soil samples, samples can be extracted in relation to a reference point (e.g., distance from surface, distance from plant, etc.). In relation to plant components, samples can be taken from a reference (e.g., distance from leaf, distance, from node, distance along root, etc.). In variations in which multiple samples are taken, samples can be pooled (e.g., combined) or kept distinct.

In relation to step S110, samples can be acquired once, or at several time points within a time period or in relation to a process (e.g., process associated with crop handling, fermentation process, process for preparing crops for consumption, etc.). The time period can be on the order of seconds, minutes, hours, days, months, years, decades, or of any other suitable time scale. In one example, samples were taken at four time points from planting to harvest. However, samples can be taken prior to planting and/or post-harvest.

Furthermore, samples can be received from one or more metacommunities, where a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, features, insights, and actions implemented in subsequent steps of the method can be generated or performed at the metacommunity level and/or at local levels of abstraction.

In one example, step S110 involved reception/collection of soil samples from vineyards from multiple geographic locations (e.g., U.S, Spain) over a certain time period (e.g., years). In the example, the samples were taken from topsoil, at a 30 cm distance from the vine trunk, within a depth between 5-10 cm.

In other examples, however, samples can be acquired in another suitable manner or from other suitable sources.

In relation to step S110, some approximation of the whole method 100 can be run with only latitude and longitude information in the absence of samples. With geostatistical models and Markov processes, the sample characteristics can be predicted without physical sampling, and the method 100 can be subsequently run to provide an ecological picture of the unknown soil. All available information can be modeled while missing information can be imputed implicitly with Bayesian models.

2.2 Methods—Sample Processing

Step S120 recites: generating a sample dataset upon processing the set of samples with a set of sample processing operations, which functions to process raw sample material with one or more operations, thereby generating base data from which features can be extracted in subsequent portions of the method. In step S120, processing the set of samples can include wet lab processing techniques (e.g., sample lysis, sample enrichment, sample purification, target material capture or separation, target amplification, etc.), as well as sequencing and library preparation operations. As such, generating sample data in step S120 includes a combination of sample processing techniques (e.g., wet laboratory techniques) and computational techniques (e.g., utilizing tools of bioinformatics) to quantitatively and/or qualitatively characterize the microbiome, functional features, and/or other aspects (e.g., chemistry) of each sample of the agricultural site(s). Sample processing operations can include generation of one or more of: a full metagenomic dataset, a metatranscriptomics dataset, and a proteomics dataset.

As such, in variations, step S120 can include one or more of: sample pre-processing (e.g., with homogenization or chopping, with use of a buffer, with formation of a pellet, etc.), sample storage (e.g., at appropriate conditions prior to subsequent processing, e.g., at −80 C, at 4 C, at another suitable temperature, etc.); sample lysis (e.g., using physical methods, using chemical methods, using biological methods, etc.); genetic material (e.g., nucleic acid material) extraction including extraction of DNA, RNA, nucleic acid fragments, or other nucleic acid material; protein extraction; nucleic acid purification (e.g., using precipitation, using liquid-liquid based purification, using chromatography, using binding moiety functionalized particles, etc.); target material capture; removal of sample waste; target incubation; target amplification (e.g., using polymerase chain reaction (PCR)-based techniques, using helicase-dependent amplification (HDA), using loop mediated isothermal amplification (LAMP), using self-sustained sequence replication (3SR), using nucleic acid sequence based amplification (NASBA), using strand displacement amplification (SDA), using rolling circle amplification (RCA), ligase chain reaction (LCR), etc.); target enrichment; and/or any other suitable sample processing steps.

In relation to amplification of nucleic acids, primers used can be designed to mitigate amplification bias effects, as well as configured to amplify nucleic acid regions/sequences (e.g., of the 16S region, 18S region, the ITS region, etc.) that are informative taxonomically, phylogenetically, in relation to emergent properties, for formulations, and/or for any other suitable purpose. Primers used in variations of Block S120 can additionally or alternatively include incorporated barcode sequences, unique molecule identifiers, adaptor sequences, or other sequences specific to each sample and/or in association with sequencing platforms, which can facilitate identification of material derived from individual samples post-amplification. Examples of custom primers are described in WO 2017/096385 published 8 Jun. 2017, which is herein incorporated in its entirety by this reference.

Furthermore, sequencing can be performed in coordination with a next generation sequencing platform (e.g., Illumina™ sequencing platform) or other suitable sequencing platform (e.g., nanopore sequencing platform, PacBio platform, MinION platform, etc.). Additionally or alternatively, any other suitable sequencing platform or method can be used (e.g., a Roche454 Life Sciences platform, a Life Technologies SOLiD platform, etc.). Additionally or alternatively, sample processing can implement any other step configured to facilitate processing (e.g., using a Nextera kit) for performance of a fragmentation operation (e.g., fragmentation and tagging with sequencing adaptors) in cooperation with amplification. Additionally or alternatively, filtering of sequences (e.g., chimeric sequences, other sequences, etc.) can be performed in coordination with step S120.

In examples of sample processing according to step S120, soil samples were stored at −80° C. in buffer until performance of a nucleic acid extraction operation (e.g., DNA extraction), where nucleic acid extraction was performed using a kit for extraction of organism DNA (e.g., DNeasy PowerLyzer PowerSoil Kit™, Qiagen™). Libraries were then prepared following a two-step PCR protocol (e.g., associated with an Illumina™ platform and protocol), and sequenced on an Illumina MiSeq™ platform using paired end sequencing (e.g., at 2×300 bp). Post-sequencing, a library preparation operation was performed, where libraries were generated upon amplification and sequencing of target regions (e.g., 16S rRNA V4 region, the ITS1 region, etc.) using custom primers as described above, and raw sequences were analyzed using VSEARCH using default parameters. Briefly, raw paired-end FASTQ sequences (forward and reverse paired reads) were merged, filtered by an expected error 0.25, dereplicated, and sorted by size. A filtering operation was performed where chimera sequences were filtered out in coordination with clustering of non-singleton sequences into 97% identity operational taxonomic units (OTUs), or into amplicon sequence variants using a single mismatch (99.7% identity). Taxonomic annotation was performed (e.g, using a SINTAX algorithm, using algorithms that implement k-mer similarity metrics to identify top taxonomic candidates for annotation, using algorithms that identify full-length alignments to reference sequences, etc.). In one example, all combined sequences were then mapped to a list of 31,516 OTUs with an identity threshold (e.g., at least 90% identity, at least 95% identity, at least 97% identity, at least 99% identity, etc.), resulting in an OTU table with 54,738,544 sequences, averaging 156,395 sequences per soil sample. Samples had only a fraction of OTU richness, averaging 529 OTUs (e.g., in relation to a range of 23-4999 OTUs) per soil sample. OTUs were then classified (e.g., with a UNITE database according to a UTAX pipeline, with a SILVA123 database through a SILVA-NGS pipeline). However, variations of the example can implement other sequencing protocols, OTU mapping, OUT classification algorithms, and/or other methods.

In variations, the method can additionally or alternatively include processing and assessment of amplicon sequence variants (ASVs). In particular, during sequencing, it is expected that some "identified" nucleotide sequences may be incorrect due to sequencing errors; thus, the reads are clustered together to compensate for this, grouping similar sequences to form clusters which are represented by the centroid sequence (i.e., the most abundant sequence of the cluster). In situations where a 97% sequence identity threshold for OTUs is too inclusive for some families of species, processes of the method can include clusterization between sequences with a difference of only one nucleotide, in order to maintain the highest possible granularity and keep small differences visible, such that they can be annotated separately. As such, the method can include performing an amplicon sequence variant operation involving: clustering of the set of identified sequences into a set of clusters; and identifying, for each of the set of clusters, a centroid sequence representing a most abundant sequence of a respective cluster of the set of clusters. Clustering the set of identified sequences can include grouping sequences of the set of identified sequences having a difference in nucleotides satisfying a threshold condition (e.g., a difference less than 1 nucleotide, a difference less than 2 nucleotides, a difference less than 3 nucleotides, a difference less than 10 nucleotides, etc.).

Thus, in certain variations, ASV-associated approaches can significantly increase the number of final sequences to annotate for the same sample, increasing resolution and allowing better discrimination of closely related species. This approach can also allow performing of annotation of ASVs against curated taxonomic databases based on exact sequence matches which allows assessing in silico performance metrics for the annotation of each ASV. In specific applications, 16S ASVs provided suitable performance metrics (e.g., >90% sensitivity, >90% specificity, >90% positive predictive value, >90% negative predictive value) for identifying ~46% of the species and ~89% of the genera. ITS ASVs also provided good performance metrics for identifying ~87% of species and ~97% of the genera.

In variations, Bayes factors derived from the posterior odds of a connection between OTUs or ASVs can be used as edge-weights for weighted directed networks, and derivative features processed by models associated with the methods.

In relation to sample acquisition and sequencing, sample data can be tagged with contextual data, in order to couple identified sample features with various conditions (e.g., perturbations, products, environmental conditions, etc.) in downstream steps of the method. In variations, contextual data can include one or more of: geographic location (e.g., latitude, longitude, altitude); meteorological metadata (e.g., from Dark Sky API); climatic information (e.g., precipitation intensity, precipitation probability, maximum temperature, minimum temperature, dew point, humidity, environmental pressure, wind speed, wind bearing, wind gust, cloud cover, UV index, etc.); environmental disaster information (e.g., fires, hurricanes, tornadoes, earthquakes, temperature variations, etc.); organic management practices (e.g., integrating cultural, biological, and mechanical practices that foster cycling of resources, promote ecological balance, and conserve biodiversity without use of synthetic fertilizers, sewage, irradiation, and genetic engineering); non-organic management practices; use of synthetic fertilizers; use of natural fertilizers; biodynamic management practices (e.g., with generation of their own fertility through composting, integrating animals, cover cropping, and crop rotation); conventional management practices (e.g., with standard farming systems, using a variety of synthetic chemical fertilizers, pesticides, herbicides and other continual inputs, etc.).

In variations, perturbations associated with the agriculture site(s) and/or crops from which samples are derived can include one or more of: a management practice (e.g., a conventional management practice, an organic management practice, and a biodynamic management practice); a regenerative practice (e.g., application of one or more of a cover crop, silvopasture, managed grazing, intercropping, etc.); a biological input including one or more of: a biostimulant, a biofertilizer, a biocontrol agent, a biopesticide, compost, and a biodynamic preparation (wherein the biological input is applied by one or more of: a broadcast spray, an in-furrow spray, seed treatment, application to soil with incorporation, and application to soil without incorporation, etc.); a natural ecological disturbance; and another suitable perturbation.

Data can additionally or alternatively be tagged with metacommunity descriptors, thereby tagging sequence data of the sample dataset with a set of metacommunity descriptors corresponding to a set of communities within a same habitat associated with the agriculture site. In particular, a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, in subsequent steps of the method 100, computing architecture for merging the metacommunity-inferred associations into each of the local communities associated with the set of samples, enables returning of estimations of network properties in all the local communities within the metacommunity, individually, obtaining sample(site)-specific information on microbial ecosystem functioning. Such processes also enable direct comparison among network properties of individual samples, even in the absence of common taxa among them, as all samples are mapped back to the metacommunity, thereby providing a normalization step. Thus, these emergent properties can be implemented as machine-determined universal biomarkers of ecological disturbance.

In relation to model architecture associated with training and refinement of machine learning models described further below, the method described in relation to step S120 can be used to create training sets of data, in coordination with step S130 below. As such, training data covering specific sample features and corresponding contextual information related to management practices and other perturbations (e.g., use of various products, environmental perturbations, other agricultural inputs, other practices, etc.) can be used to refine models for predicting effects of various practices and perturbations, and to guide future management practices in a sustainable manner.

In order to process such data, computing platforms implementing one or more portions of the method can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions. However, step S120 can be performed using any other suitable system(s).

2.3 Methods—Data Transformation for Extraction of Features

Step S130 recites: generating a set of microbiome-associated features upon performing a set of transformation operations upon the sample dataset, which functions to extract features associated with network properties of sequences associated with organisms. For instance, transformations can be associated with functional inference based on the taxonomic abundances and the known genetic composition of the microorganisms identified, as well as ecological network factors with operations for comparing functions and ecological network properties has a higher degree of universality and thus allows more robust comparisons.

Step S130 can additionally or alternatively generate microbiome composition/community features (e.g., in relation to taxonomical features), as described above. As such, step S130 can be used to generate features that can be processed by models generated and trained as described below, in order to better understand the ecological processes and mechanisms behind community assembly. These processes are envisaged to be a collection of inter- and intraspecies interactions, which are represented by a network (formally, a graph in discrete mathematics). In subsequent steps, structural properties of such networks and their relationships can be contextualized as emergent properties, which can be used to characterize statuses and responses to perturbations with respect to the agriculture site(s) being assessed.

In more detail, step S130 functions to generate features that go beyond Community Aggregated Traits (CATs) associated with constituent taxa of the set of samples, by generating features based upon emergent properties that arise from specific community arrangements. Such emergent properties are then processed to generate insights related to the functionality of crop communities (e.g., seed survival rate), microbial communities (e.g., biofilm density, as a cause of composition behaviour), and/or other communities in subsequent steps.

In relation to step S130, the computing platform described can process outputs of step S120 to generate a community dataset characterizing communities of organisms associated with the sample(s) acquired in step S110. Generating the community dataset can include one or more of: rarefying samples to a desired sequencing depth in order to provide a desired level of detectability of OTUs of the sample(s); filtering OTUs with a desired threshold condition (e.g., retaining OTUs represented in a threshold number of samples); implementing a test for assessing that local communities are represented adequately (e.g., using a Mantel test of Bray Curtis dissimilarities); transforming one or more data outputs derived from step S120 to include presence and absence factors with respect to co-inclusion and/or co-exclusion of individual species (or other taxonomic units); rescaling of counts such that compositional data which is bounded in the [0, 1] interval, i.e. a relative abundance, can be represented on the full number line, ranging from negative infinity to positive infinity; retrieving significant co-inclusion and co-exclusion properties (e.g., for samples associated with individual sites, independently of each other), in order to provide data representing potential for interactions in complete metacommunity and/or environmental distributions (e.g., thereby generating a first grouping of positive pairs of organisms and a second grouping of negative pairs of organisms); and performing other suitable data transformation steps.

Then, to generate a network property dataset, the computing platform described can process the community dataset with architecture for implementing one or more processes including: transforming the first grouping of positive pairs of organisms and second grouping of negative pairs of organisms (related to co-inclusion and co-exclusion, respectively) into one or more aggregate matrices representing the possibility of co-inclusion (e.g., the whole number of potential associations between all the taxa in the pool, associations that are described as system relevant interdependencies including: biotic interactions, environmental affinities, dispersal restrictions, etc.) and co-exclusion of species (or other taxonomic units) in the metacommunity(ies) associated with the set of samples; subdividing the one or more aggregate matrices into a set of individual matrices containing features associated with only the species (or other taxonomic units) occurring in each of the set of samples; performing co-inclusions and/or co-exclusion estimations in another suitable manner (e.g., based upon covariance determination methods, based upon correlation determination methods, with SparCC, with SPIECeasi, etc.); processing the set of individual matrices in order to generate a set of undirected network mappings with nodes representing species (or other taxonomic units) and edges representing statistically significant co-inclusions/co-exclusions; and performing other suitable data processing steps. Then, in relation to step S130, the computing platform can implement architecture for extracting features from the set of undirected network mappings, where features can include one or more of: a number of connected components (i.e., defined in relation to a subnetwork in which any two nodes connect to each other by edges, that lack connection to other nodes in the full network); a modularity factor (e.g., a quality of a partition into modules such as groups of nodes using a quantity of edges inside modules compared to a quantity of edges between modules, using an appropriate clustering algorithm (e.g. walktrap, Louvain, fast greedy, edge-betweenness, etc.); a clustering coefficient (e.g., based upon a transitivity determination and defined as a the ratio of triangles to connected triples in a respective network); an average path length between network components (i.e., defined as a mean of the minimal number of required edges to connect any two nodes); an assortativity factor (e.g., a feature which measures homophyly of a network, according to node properties or labels such as node degree, which quantifies the number of edges associated to a node); a proportion of co-inclusion factor normalized to a total number of combinations of all OTUs in the sample(s); a proportion of co-exclusion factor normalized to a total number of combinations of all OTUs in the sample(s); and other suitable features. In variations, networks can be visualized or rendered by the computing platform, in order to generate depictions of network topology in multidimensional space (e.g., in relation to generation of reports or execution of actions described in further detail below).

As described above, step S130 can also generate features associated with compositional aspects and/or functional aspects of the sample(s) from the agriculture site(s). For instance, compositional and functional aspects can include compositional aspects at the microorganism level, including parameters related to distribution of microorganisms across different groups of kingdoms, phyla, classes, orders, families, genera, species, subspecies, strains, infraspecies taxon (e.g., as measured in total abundance of each group, relative abundance of each group, total number of groups represented, etc.), and/or any other suitable taxa. Compositional and functional aspects can also be represented in terms of operational taxonomic units (OTUs), amplicon sequence variants (ASVs) or other units. Compositional and functional aspects can additionally or alternatively include compositional aspects at the genetic level (e.g., regions determined by multi-locus sequence typing, 16S sequences, ITS sequences, other genetic markers, other phylogenetic markers, etc.). Compositional and functional aspects can include the presence or absence or the quantity of genes associated with specific functions (e.g., enzyme activities associated to nutrient metabolism, disease resistance, biocontrol microorganisms and metabolites, stress sensing and resistance microorganisms and metabolites, phytohormone production, etc.).

In a specific example related to abundance-associated features, step S130 included implementation of methods for determining differential abundance of various OTUs. In more detail, zero counts in data were replaced, where valid values for replacement were calculated under a Bayesian paradigm, assuming a Dirichlet prior. Non-zero values were then adjusted to maintain the overall composition using a pairwise comparison process for differential expression analysis (e.g., edgeR algorithm). For each OTU, the fold change attributable to a treatment (e.g., biostimulant) across different times (e.g. T0 to T1) was calculated. This was done by conducting a hypothesis test separately for each location, measuring the fold change of a given OTU in the treatment group (from T0 to T1) vs. the fold change in the control group (from T0 to T1), and then repeating the test but using times T0 and T2.

In variations, network properties can be determined for different types of organism communities (e.g., bacterial communities, fungal communities, etc.) independently of each other or in an aggregated manner.

Network properties can further include local network features extracted from a metacommunity network, and network properties from co-exclusion networks and network properties from co-inclusion networks.

Network property determination can further include estimating network properties from a given RNA-seq sequencing sample by way of: estimating a meta-network from the entire sample dataset, estimate the local network as an induced subgraph at the sample level of the bigger meta-network graph, and calculating its network properties, where each network is considered a collection of pairwise connections. Features can be derived from combinations of p-hypergeometric (PH) network properties and Bayesian factor (BF) network properties (and/or Bayesian fisher network properties, Monte Carlo Markov Chain network properties, other properties) and can include one or more of: transitivity properties, modularity properties, assortativity properties, total number of species represented, and other suitable properties.

In examples, p-hypergeometric (PH) network operations performed can implement assumptions that the co-occurrence of two events that are not dependent follows a hypergeometric distribution. In examples, an occurrence is defined as a count above 0. Hence, for a given pair OTU counts, a co-occurrence is when both have a count >0 in the same sample. The probability of observing the pattern of co-occurrences across the whole dataset is tested against the theoretical hypergeometric distribution (hence the name p-hypergeometric, or PH network). Pairs of OTU occurrences that happen significantly more times than would be expected by chance are labelled as a co-inclusion connection. Conversely, pairs of occurrences that happen significantly fewer times than would be expected by chance are labelled as having a co-exclusion connection.

In examples, Bayesian factor (BF) network operations performed can implement assumptions that do not consider 0 to be a threshold value. Instead counts themselves are classified. For example, in a given sample a first OTU of a pair has 20 reads and a second OTU of a pair has 50 reads. The "common count" or CC is 20 reads (by definition, always the minimum of the two). The absolute difference or AD between them is 30. In BF operations, the "balance" between these two counts for every pair of OTUs possible (In practice, we measure the odds of seeing the current distribution of CC and AD) is measured. To generate the network operations include generating a Bayesian factor for each sample for the odds of co-occurrence of any given pair. Since the BF is a continuous number, filtering can be performed at any point. In an example, filtering can be performed at BFmedian >1.2 for co-inclusion and BFmedian<0.8 for co-exclusion.

Furthermore, additional interactions characterized between organisms can include commensalism factors, facilitation factors, mutualism factors, antagonism factors, competition factors, neutralism factors, and amensalism factors, which are derived from combinations of positive, negative, and neutral interactions.

2.3.1 Statistical Analyses

In variations, features can additionally or alternatively be processed with one or more statistical or other mathematical processes, in order to generate derivative features derived from outputs of steps S120 and/or S130. For instance, processing of features can include one or more of: implementation of principal component analysis (PCA) methods; generating measurements of variance; implementation of correlative tests (e.g., Spearman correlations); implementation of variance tests (e.g., Kruskal-Wallis tests); implementation of multidimensional scaling processes (e.g., a non-metric multidimensional scaling (nMDS) algorithm); performing probabilistic methods; implementation of statistical models (e.g., generalized linear models, etc.); and performing other suitable statistical tests.

In examples, the method can include steps for performing alpha-, beta-, and/or gamma-diversity analyses in relation to various taxonomic groups and/or associated features. For instance, variations of the method include steps for performing alpha- and beta diversity analyses using 16S and ITS ASV or OTU counts (e.g., using R vegan), where alpha-diversity metrics (e.g., Shannon, richness, etc.) were calculated and plotted across all covariates available. The algorithm also implemented architecture for performing Wilcoxon rank-sum tests to compare samples associated with different treatments (e.g., control and treatment groups) within location-timepoint subgroups. For beta-diversity, the algorithm implemented Kruskal's non-metric multidimensional scaling in conjunction with Aitchison distances. The algorithm also implemented architecture for determining relative abundances for OTUs as well as generating annotations at various taxonomic levels (e.g., genera, families, etc.), for use in subsequent analyses. The algorithm also implemented architecture for performing permutational multivariate analysis of variance on the Aitchison distance matrix, using all possible combinations of the location, timepoint and treatment variables.

However, other variations of methods for characterizing diversity metrics and/or other statistical methods can be implemented.

2.3.2 First Example of Generation of Network Properties

In a first example of generation of network properties informative of agriculture site characteristics and ultimately crop-associated features, step S130 included building a metacommunity network of all samples with architecture for: estimating the co-occurrence and co-exclusion that would occur solely by chance for all possible OTU pairs. The algorithm also implemented architecture for selecting OTU pairs that occurred significantly more than expected by chance to create the co-occurrence networks. Similarly, those that occurred significantly fewer times than expected by chance were used to build the co-exclusion network. Local networks (e.g., single sample-level) were calculated by subsetting the metacommunity network for OTU pairs detected in each sample and estimating a local network. The algorithm also implemented architecture for calculating network properties, according to methods described, where network properties were compared using a linear model. Using the network property as outcome, hypothesis tests were performed to compare timepoint differences in various sample groups (e.g., treated vs. control group), in a manner analogous to the approach used for investigating differential abundances described above.

Other examples of generation and use of network properties are described in U.S. application Ser. No. 17/119,972 filed 11 Dec. 2020, which is herein incorporated in its entirety by this reference.

2.4 Methods—Model Development and Use

Step S140 recites: returning an analysis characterizing the set of crop-associated features based upon the set of microbiome-associated features. Step S140 functions to implement feature data as inputs, and to generate outputs corresponding to crop-associated features (e.g., estimations of predicted yield, etc.). Step S140 can additionally or alternatively be used to predict or characterize agriculture site statuses and/or responses to various perturbations with respect to downstream applications.

In relation to estimations or other predictions returned using step S140, computing platform subsystems described can implement architecture for processing features, generating network data, providing insights, with training of models by processing suitable training datasets. In particular, the emergent properties and/or other features described, given the ultra-high dimensionality of microbiome data, are not practically detectable by the human mind, and are instead trained and processed by the machine learning architecture in relation to associated steps of the method 100.

Figure 2:
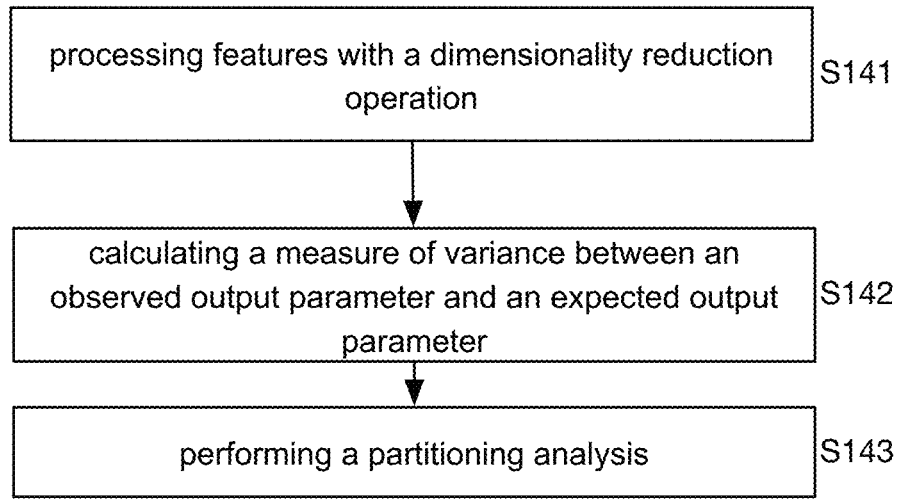
FIG. 2 depicts an embodiment of a portion of a workflow of a method for evaluating and predicting crop features.

In one aspect, as shown in FIG. 2, a generated model can include architecture for processing features (e.g., estimates of alpha-, beta-, and/or gamma-diversity, co-inclusion features, co-exclusion features, other features described above) as inputs, and returning derivative outputs describing crop-associated features, where processing of input features can occur at multiple layers of the model(s) in relation to model architecture.

In variations, crop-associated features can include one or more of: yield characteristics, crop health and disease states, crop age characteristics (e.g., lifespan, cycles of productivity, vegetative growth state, etc.), crop shelf life, and/or other crop-associated characteristics. As such, embodiments of the method can include steps for predicting crop yield based solely upon microbiome characteristics of samples acquired from the agricultural site associated with the crops.

Additionally or alternatively, in variations, outputs of step S140 can include one or more of: nutritional composition features (e.g., of soil) at the agriculture site, soil carbon sequestration characteristics, and other features associated with the agriculture site.

As shown in FIG. 2, generation of crop-associated and/or other features can include: processing first features with a dimensionality reduction operation S141 (e.g., PCA) as described above. Then, in order to evaluate the degree in which local network properties deviate from a null model expectation (e.g., based upon an expected unperturbed state sampled from similar sites), the computing platform can include architecture for processing matrices containing only the species occurring in each of the individual samples, which were randomized across the metacommunity co-inclusion/co-exclusion matrices.

The computing platform can then, as shown in FIG. 2, include architecture for calculating a measure of variance between an observed output parameter and an expected output parameter S142, followed by assessment if a factor (e.g., agricultural input, weather, management, applied product, etc.) had an effect on network properties (e.g., through Spearman correlations, through Kruskal-Wallis tests, regression models, machine learning algorithms, etc.) as described above.

To estimate the relative contribution of an input factor and/or other characteristic related to the crop-associated factor, network properties, and/or other properties, the computing platform can include, as shown in FIG. 2, architecture for performing a partitioning analysis S143 using the non-metric multidimensional scaling (nMDS) two-dimension scores as the response variables.

In variations, the computing platform can include architecture for calculating predicted crop-associated features (e.g., yield) and/or other crop or agriculture site characteristics, by fitting variables derived from features described above (e.g., in relation to a transitivity feature, in relation to a modularity feature, in relation to an average path length, feature, in relation to a co-exclusion proportion parameter, etc.) into a generalized linear model (GLM) with a suitable distribution (e.g., a binomial distribution) as well as non-parametric (e.g. kernel regression, k-nearest neighbours, etc.) and machine learning (e.g. random forest, LASSO-Ridge regression, etc.) models.

As such, architecture of the systems described in relation to step S140 can process input features and return outputs that are indicative of statuses and responses to various perturbations, which can be used in downstream portions of the method 100 in order to improve or maintain characteristics of the agriculture site(s) being analysed in a desired and/or sustainable manner.

With further training, advanced models can further be configured to generate crop-associated feature predictions based on microbiome-derived data, without knowledge of other information, in order to characterize aspects of the agriculture sites and/or crops.

2.4.1 Models and Machine Learning Approaches

To refine the model(s), the method 100 can include generating one or more training sets of data, from samples of the agriculture site(s) and/or other samples of other agriculture site(s), in order to train the artificial intelligence (AI)/neural network (NN) model(s) in one or more stages of training, to identify features of interest from various inputs. In variations, generating training sets of data can include processing raw data and/or features taken from agriculture sites and/or crops with known characteristics (e.g., in relation to contextual and/or other data described above, in relation to agricultural inputs/practices applied in substantially controlled settings, etc.). Such training data can be tagged with associated crop-associated features, agriculture site statuses (e.g., health statuses) and/or other information (e.g., pertaining to nature of inputs/practices, etc.).

In examples, training data can include tagged contextual information, which can include environmental information, geolocation information, nature of products applied (e.g., dosing, duration of application, frequency of application), pathogens present at a site, and/or other suitable information.

Figure 3:
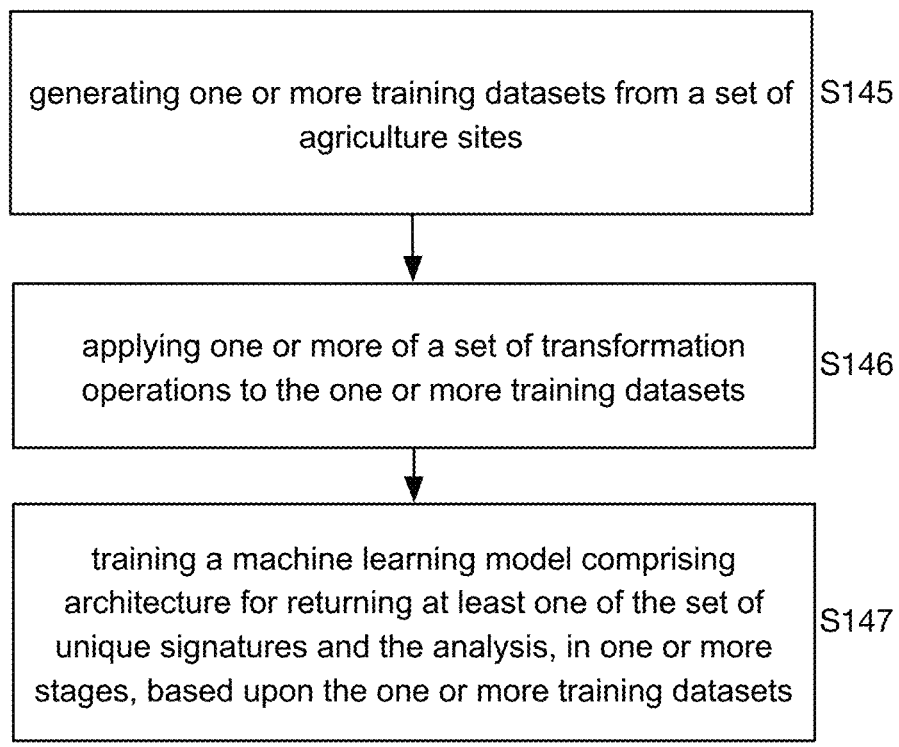
FIG. 3 depicts an embodiment of a portion of a workflow of a method for evaluating and predicting crop features with respect to training and refining developed models.

Training sets of data can include raw sequencing data, transformed sequencing data (e.g., according to transformation operations described above), and/or other suitable data. As such, as shown in FIG. 3, the method 100 can include: generating one or more training datasets S145 from a set of agriculture sites and/or crops (e.g., sites different from those in step S110, sites overlapping with those in step S110), the training datasets corresponding to features (e.g., of emergent properties, of community properties, of taxonomic properties, of functional properties, etc.) in association with statuses and/or inputs or practices experienced by the agriculture site(s) and associated crops; applying one or more of a set of transformation operations to the one or more training datasets (e.g., using one or more operations described above) S146; and training a machine learning model comprising architecture for returning at least one of the set of unique signatures and the analysis, in one or more stages, based upon the one or more training datasets S147. Additional details are provided below.

For instance, in relation to generation of training datasets, the method can include generating network properties/emergent properties and other features upon samples from agriculture sites (or other sites) where statuses and/or perturbations are known. Additionally or alternatively, first training datasets can be generated from network properties/emergent properties and other features upon processing samples from agriculture sites (or other sites) known to be at baseline state. The model can be trained based upon the first training datasets. Then, the site(s) and/or associated crops can be intentionally perturbed in some manner, with subsequent sample acquisition and processing used to generate second training datasets for refining the model. This process can be repeated any suitable number of times. As such, training data can be developed in multiple stages. In relation to multiple stages of training, the method 100 can refine models based upon incorrect classification of outputs (e.g., mis-characterized statuses and/or perturbations).

Furthermore, combinatorial features (e.g., combination features derived from one or more individual network properties, one or more community properties, one or more taxonomic properties, and/or other suitable properties) can be used for training. In more detail, features may be transformed either individually or in combination before being processed by the model(s). As an example of an individual feature transformation, a feature derived from a transform of a co-exclusion feature might be used instead of or in addition to the co-exclusion feature itself. As an example, a combinatorial feature can be derived from synchronous co-exclusion of a pair of organisms and co-inclusion of a pair of organisms (e.g., where occurrence together is a feature). Additionally or alternatively, combinatorial features based upon bacteria-associated parameters and fungal-associated parameters can be used as inputs (e.g., as a unified "impact" parameter or feature). For instance, an impact parameter can be derived from the scaled dissimilarity (distance) between the network properties (e.g., 16S network properties, ITS network properties), as described in U.S. application Ser. No. 17/119,972 filed 11 Dec. 2020, incorporated by reference above.

Additionally or alternatively, dynamic aspects (e.g., changes over time in features, changes in frequency between instances of respective features, other temporal aspects, other frequency-related aspects, etc.) of features derived from the samples can be used to predict or otherwise anticipate statuses. As such, models can be implemented to prevent adverse statuses of the agriculture sites to prevent root causes of failure and/or break chains of events that could lead to a cascade of agriculture site problems.

Models can be developed and trained for real-time analyses and/or historical analyses. In relation to real-time analyses, the models can be refined for rapid classification (e.g., with node reduction, with reduced thresholds, with lower confidence, etc.). In relation to historical analyses, the models can be refined for detailed classification (e.g., without node reduction, with higher thresholds for classification predictions, with higher confidence, etc.).

In embodiments, the method 100 can thus include training a model configured to process input features and return predicted characterizations of crop-associated features and/or other features of the agriculture site, wherein training the model comprises: collecting a training dataset derived from training samples, the training dataset corresponding to training samples subject to at least one of the management practice and the perturbation to the agriculture site as well as control samples without undergoing the input factor; applying one or more of a set of transformation operations to the training dataset; and training the model with the training dataset, the model comprising architecture for returning the analysis, in one or more stages.

While embodiments, variations, and examples of models (e.g., in relation to inputs, outputs, and training) are described above, models associated with the method 300 can additionally or alternatively include other blocks for statistical analysis of data and/or machine learning architecture.

Statistical analyses and/or machine learning algorithm(s) can be characterized by a learning style including any one or more of: supervised learning (e.g., using back propagation neural networks), unsupervised learning (e.g., K-means clustering), semi-supervised learning, reinforcement learning (e.g., using a Q-learning algorithm, using temporal difference learning, etc.), and any other suitable learning style.

Furthermore, any algorithm(s) can implement any one or more of: a regression algorithm, an instance-based method (e.g., k-nearest neighbor, learning vector quantization, self-organizing map, etc.), a regularization method, a decision tree learning method (e.g., classification and regression tree, chi-squared approach, random forest approach, multivariate adaptive approach, gradient boosting machine approach, etc.), a Bayesian method (e.g., naïve Bayes, Bayesian belief network, etc.), a kernel method (e.g., a support vector machine, a linear discriminant analysis, etc.), a clustering method (e.g., k-means clustering), an associated rule learning algorithm (e.g., an Apriori algorithm), an artificial neural network model (e.g., a back-propagation method, a Hopfield network method, a learning vector quantization method, etc.), a deep learning algorithm (e.g., a Boltzmann machine, a convolution network method, a stacked auto-encoder method, etc.), a dimensionality reduction method (e.g., principal component analysis, partial least squares regression, etc.), an ensemble method (e.g., boosting, boot strapped aggregation, gradient boosting machine approach, etc.), and any suitable form of algorithm.

2.4.2 Geographical and Phenological Stage Dynamics

In some embodiments, the methods described can thus include: collecting/receiving samples across a set of time points, and returning characterizations of evolving population dynamics within fungal and/or other organism populations at the agriculture site, based upon alpha diversity and beta diversity patterns. Additionally or alternatively, collecting/receiving samples across a set of time points can be used to evaluate effects of actions executed at the agriculture site(s), for instance, in relation to actions performed in association with repeated instances of Step S140 below. As shown in FIGS. 4A-4D, embodiments of a portion of the model returned a clear population dynamic occurring from T0 (before planting) to T1 and T2 samples (i.e., one and two months after planting, respectively) in all locations. FIG. 4A shows that in terms of beta-diversity of bacterial populations, both the location ($R^2=0.24$) and the phenological stage ($R^2=0.21$) had significant effects, with the treatment ($R^2=0.01$) having a minor non-significant effect. However, for fungal populations (FIG. 4C), location dominates as the main driver of the beta-diversity patterns ($R^2=0.36$), with the phenological state having a much lower impact ($R^2=0.08$) than in bacterial populations, and the treatment ($R^2=0.01$) showed a minor but significant effect. As shown in FIGS. 4A and 4C, a first location (e.g., White Pigeon) is significantly different from second and third locations (e.g., Grant and Sutton); this can be easily explained by the geographical distance between locations, which correlates well with the Aitchison distances of samples in the PCoA analysis. Contextual data processed also captured different edaphological and weather conditions at each of these locations, as input factors affecting diversity patterns. The significant differences between microbial community compositions before and after planting can be clearly seen at FIGS. 4A and 4C, where, despite the large differences between locations, T1 and T2 samples clustered in all the three locations, away from their respective T0, especially in the case of bacterial populations.

Figure 4B:
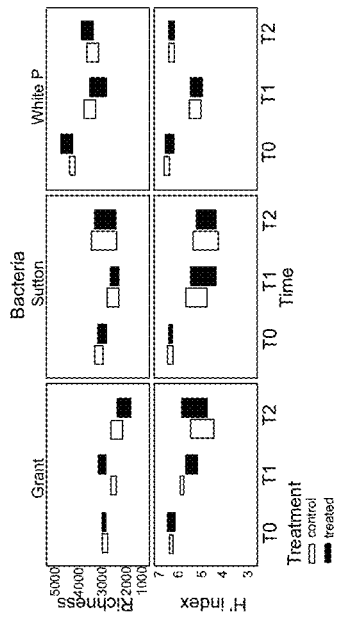
FIGS. 4A-4D depict variations of outputs of a method for evaluating and predicting crop features.
Figure 4D:
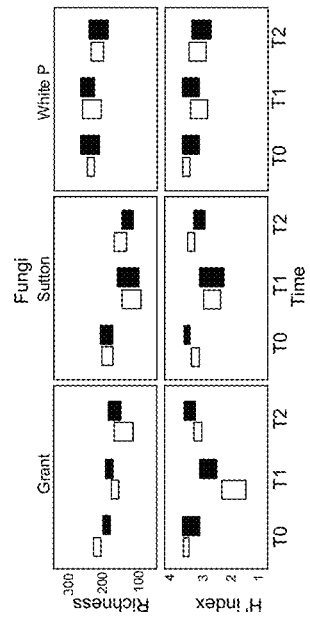
Figure 4A:
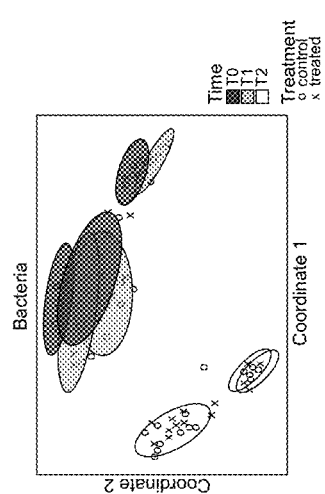
Figure 4C:
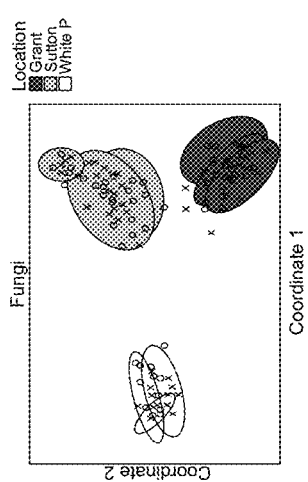

Regarding alpha-diversity FIGS. 4B and 4D, outputs of the model were used for characterizing changes in richness and diversity at the agriculture site(s). In more detail, model outputs demonstrated the impact of planting in reducing the diversity of bacterial and fungal populations, as shown for both OTU/ASV richness and Shannon (H') index values from T0 to T1 and until time T2 in most cases, indicating that the phenological stage of the plant is the main driver of changes at the alpha-diversity level in both bacterial and fungal populations. Comparing control versus treated samples at the same time point, we observed significant changes (e.g., in Grant-sourced samples) at T1 for bacterial richness and Shannon index as well as fungal Shannon index. The model also returned outputs that demonstrated that Grant was the site with the best yield increase response due to treatment. When soil samples were again analyzed after harvest (T3) in Grant and Sutton locations, there was no significant changes in alpha-diversity between the microbial communities found in the soil before planting (T0) and after harvesting (T3); therefore, the plant's associated soil microbiota seems to have cycled back to its original state.

Figures 5, 6A, 6B:
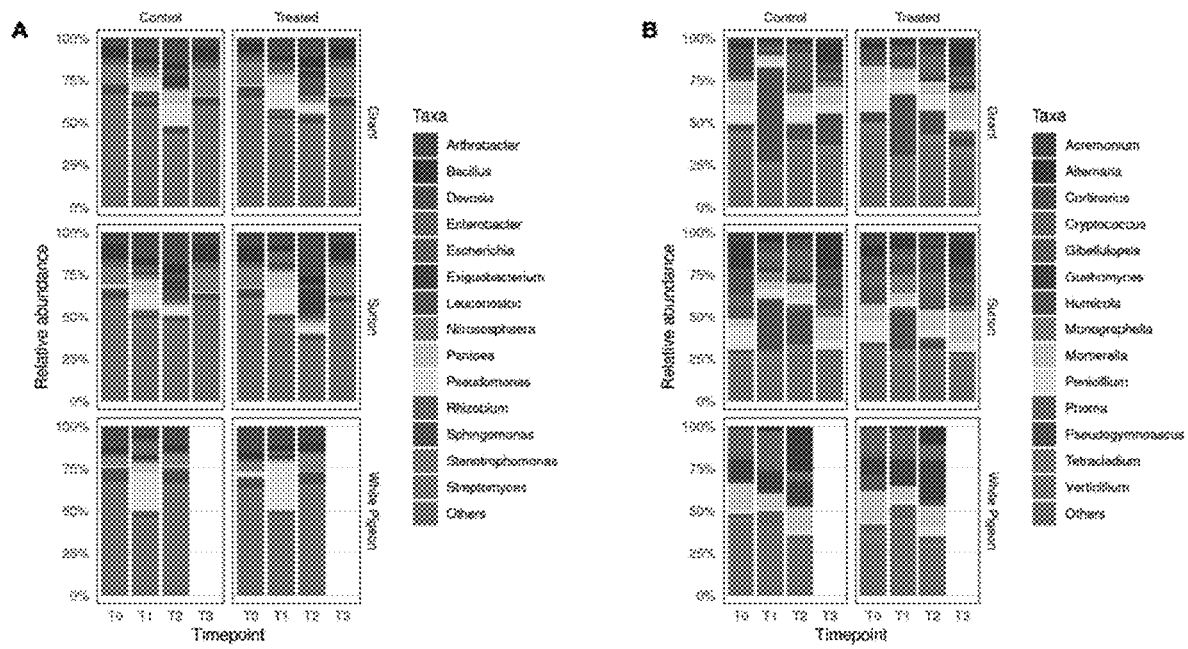
FIG. 5 depicts outputs related to relative abundance of taxonomic groups at various time points in relation to inputs associated with a method for evaluating and predicting crop features.
FIGS. 6A-6B depict outputs related to importance in yield predictions of a method for evaluating and predicting crop features.

At the taxonomy level, the model returned outputs demonstrating clear population dynamic patterns from T0 to T2 sampling times in all the three locations and in both treated and untreated samples, as well as abundant genera for both bacterial and fungal communities. FIG. 5 shows the top bacterial genera identified across samples in this study (core microbial species). Among the top fungal genera shared across samples in our study (core fungal species) we found *Cryptococcus*, *Mortierella*, and *Alternaria*. Outputs of the model also demonstrated clear temporal—cyclical—dynamics which differentiates bulk soil (T0 and T3) and rhizosphere soil (T1 and T2) samples (FIGS. 4A-4D).

2.4.3 Crop Feature—Yield in Response to a Bioinoculant Example 1

Sets of samples can be collected contemporaneously with application of a bioinoculant at the agriculture site, and returning the analysis can include returning a yield characterization of crops at the agriculture site in response to application of the bioinoculant. In one example application of methods and models described, yield was characterized for potato crops, in response to treatment by a microbial bioinoculant (*B. amyloliquefaciens* strain QST713), with evaluation of rhizosphere microbiota and bulk soil microbiota associated with acquired samples from multiple locations. In this example, treatment comprised an in-furrow application of the biological biostimulant during planting of tubers. The biostimulant contained a minimum of 2.7× low CFU/g of *B. amyloliquefaciens* QST713, and it was applied at a dose of 0.935 l/ha. However, variations of treatment can include other methods of application and/or other dosing.

In particular, yield data was first explored using medians and interquartile ranges (IQRs) of data, with rank sum tests (e.g., Wilcoxon rank sum tests) performed. The OTU counts (as described in variations of methods above) were transformed by model architecture using the centered log-ratio (CLR) transformation. CLR-transformed 16S and ITS data were jointly projected onto 70 principal components. The method was further structured to fit a Random Forest model with architecture for determining if a rhizosphere or bulk soil sample was sourced from a block with a yield ≤30t/ha or >30t/ha, based on its microbiome composition and structure using multivariate compositional data (Principal Components from a beta-diversity ordination) and local network properties. Factors derived from geographical and phenological stages (e.g., examples of which are discussed in Section 2.4.2 above) were also analyzed.

In more detail, the method was configured to measure yield data in 20 plots treated by the bioinoculant and 20 untreated plots (from multiple geographical locations), and for each we utilized all samples available over times T0, T1 and T2. In total 112 samples were processed by the example method and split into a training set of 84 samples and a test set of 28 samples. The result of this model showed a predictive accuracy of 78.6% (FIG. 6A) and identified four variables/factors (e.g., two network properties and two compositional properties) and associated values as a set of important predictors of yield (FIG. 6B), even with a higher importance than location (variable importance was based on the Gini index). The method was able to identify previously-unknown features (e.g., the structure of fungal communities, fungal co-occurrence transitivity and co-exclusion proportion, etc.) that demonstrated a much higher predictive value than the structure of bacterial communities (FIG. 6B).

The example model also returned outputs characterizing an inverse correlation between the co-occurrence transitivity of bulk and rhizosphere soil fungal communities and the yield found in the potato cultivars. Such an output provides insights into understanding the effects of agricultural inputs (e.g., of a *B. amyloliquefaciens*-based biostimulant, of other inputs, etc.) in shaping the structure of fungal communities as a potential mechanism of action when increasing the yield. Other variations of insights with actionable outcomes in relation to improving yield and/or agricultural site statuses are further described. As shown in FIGS. 7A-7C, in going from T0 to T1 the increase in fungal co-occurrence transitivity in one geographical location (e.g., Grant) is greater in the control samples than the treated ones, and in another location (e.g., Sutton) the treatment was also found to increase yield significantly. In a third location (e.g., White Pigeon) the model returned outputs indicating a decrease in fungal co-occurrence network transitivity in going from T0 to T1 in treated samples, and even a more marked decrease in control samples, corresponding to a lower yield state. Two compositional variables (PC3 and PC1) contributing to the predictive power of the model were also explored by processing taxonomy of the OTUs (e.g., fungal biocontrol agent *Trichoderma* sp.) and/or in relation to interaction patterns among various OTUs, and returning yield predictions.

In relation to the example model, yield was treated as a constant for all samples within a location and treated as a bimodal/multimodal categorical variable in relation to yield per area (e.g., bimodal as ≤30t/ha, >30t/ha; multimodal as ≤26t/ha, >26t/ha to 35t/ha, >35t/ha; multimodal as 20t/ha, >20t/ha to 26t/ha; >26t/ha to 35t/ha, >35t/ha; etc.). The example model returned outputs indicating that fungal co-occurrence transitivity and fungal co-exclusion proportion had high predictive power in relation to yield, independent of the number of yield categories used. Bacterial co-exclusion proportion, fungal co-inclusion modularity, and PC12 also demonstrated high predictive power. As such, the example model was constructed to process microbiome composition and structure data, with training of a Random Forest model to estimate if a bulk or rhizosphere soil sample came from a low or high yield block with relatively high accuracy. The example model also returned outputs indicating that the structure of fungal communities is a better estimator of potato yield than the structure of bacterial communities but that bacterial community factors and other factors had predictive power in relation to crop yield predictions, with respect to treatment and control groups.

Figure 9:
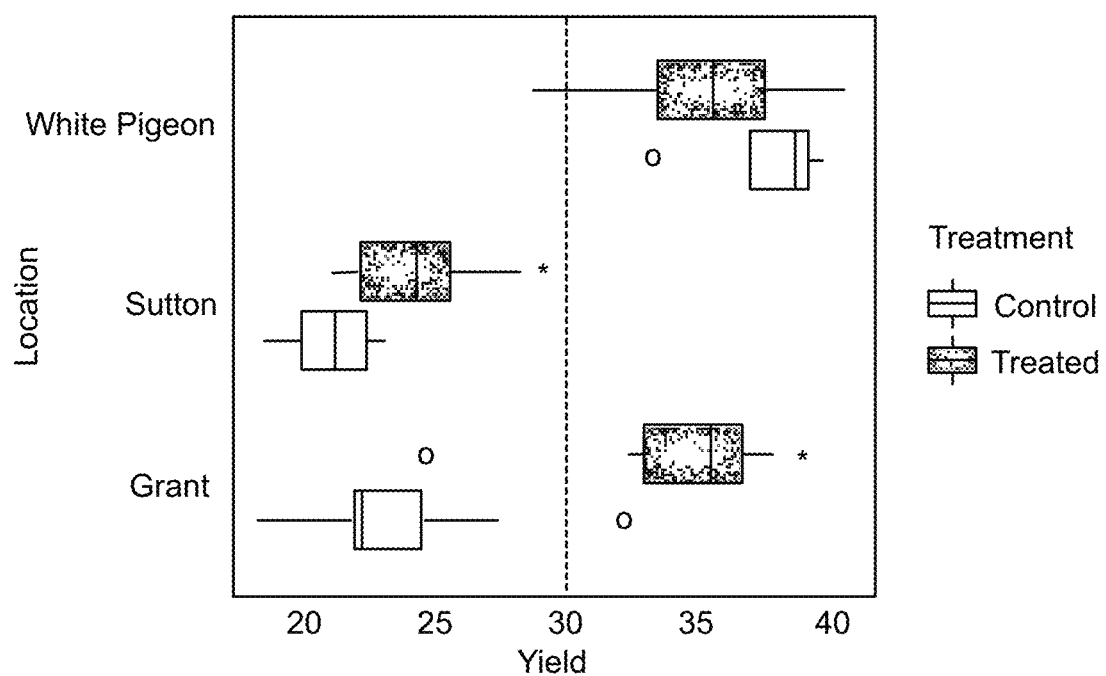
FIG. 9 depict outputs of a method for evaluating and predicting crop features in response to applied treatments.
Figure 10A:
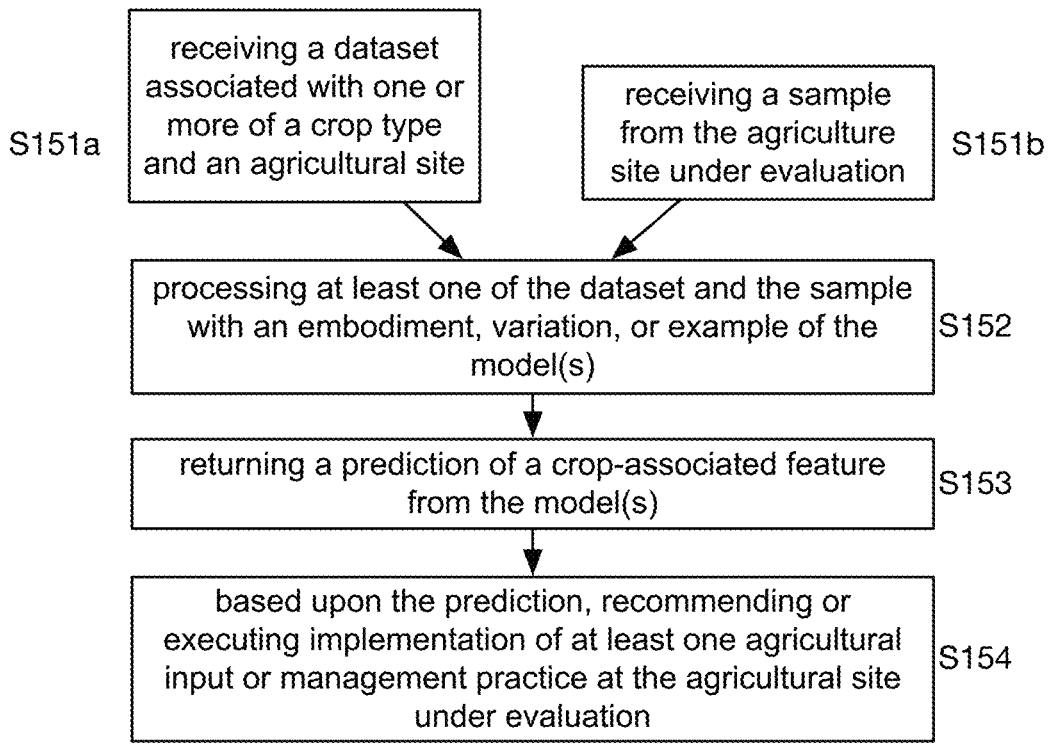
FIGS. 10A-10B depict variations of a method for evaluating agricultural inputs and practices.
Figure 10B:
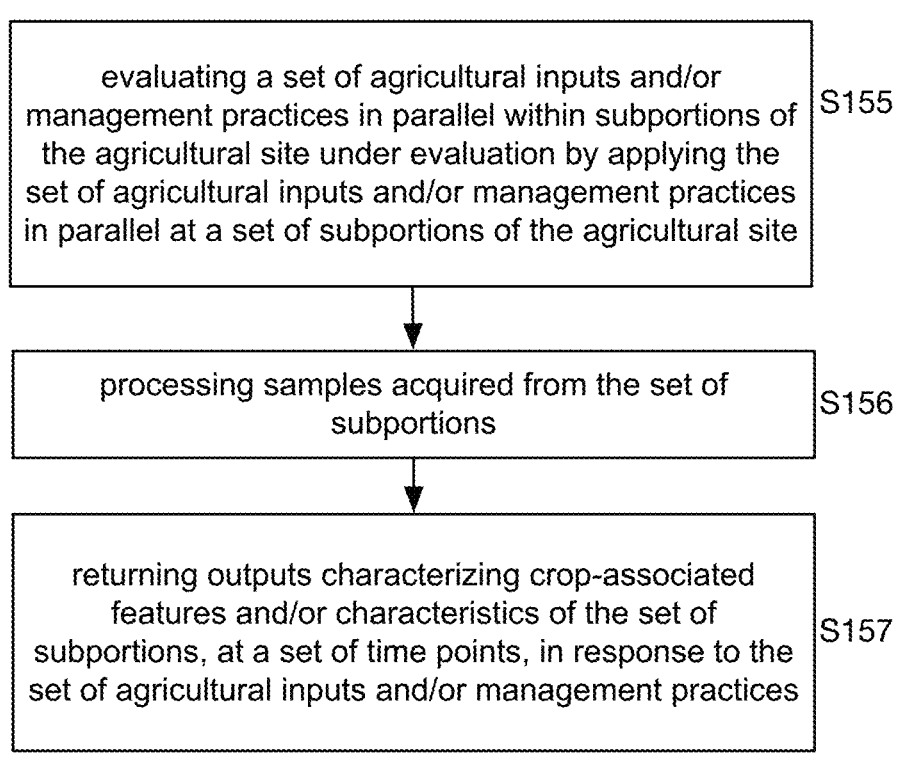
Figure 11:
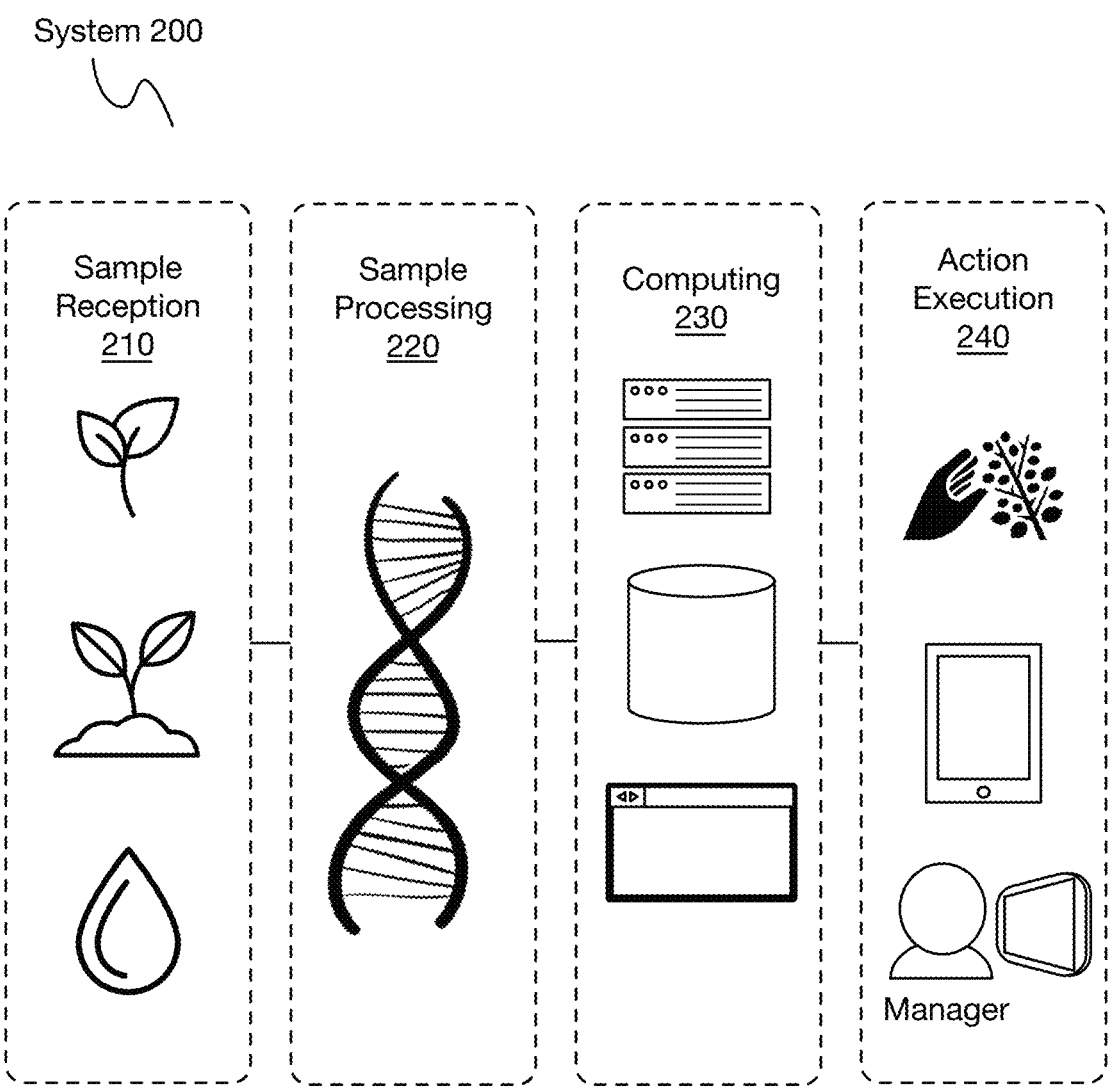
FIG. 11 depicts a schematic of an embodiment of a system for evaluating and predicting crop features.

FIG. 9 depicts outputs demonstrating that use of the bioinoculant had a significant effect on increasing the crop yield (Grant p-value $8.66 \times 10^{-10}$, and Sutton p-value $7.67 \times 10^{-7}$) in two of the three locations assayed, thereby indicating effectiveness of the bioinoculant in affecting yield at some of the agricultural sites.

Furthermore, outputs of the methods further demonstrated that use of the bioinoculant modulated microbiome composition and structure significantly, as related to yield characteristics of crops harvested from the agricultural sites. In more detail, the method included steps for determining the fold change of each OTU in the bioinoculant treatment group from T0 to T1 (and from T0 to T2) vs. the fold change in the control group at the same time intervals per location. Out of 17,241 unique bacterial OTUs in the samples of the study, 16 changed significantly from T0 to T1 (i.e., one in Sutton, and 15 in White Pigeon), and 100 from T0 to T2 (i.e., 16 in Grant, 79 in Sutton, and five in White Pigeon). These OTUs belong to 73 genera, of which, 13 changed significantly in at least two locations: *Bacillus, Bradyrhizobium, Clostridium, Novosphingobium, Rhodoplanes, Sphingomonas, Sphingopyxis*, and *Woodsholea* in Grant and Sutton; *Agromyces, Flavobacterium*, Pedobacter, and Sporosarcina in Sutton and White Pigeon; and *Stenotrophomonas* in Grant and White Pigeon. For fungi, out of 1,702 unique OTUs, ten OTUs changed significantly from T0 to T1 (i.e., eight in Sutton and two in White Pigeon), and 32 from T0 to T2 (i.e., 32 in Sutton). These OTUs belong to 30 genera, of which, one changed significantly in at least two locations: *Cryptococcus* in Sutton and White Pigeon. Thus, despite the location and phenological stage having a larger effect than treatment in the composition of microorganism populations, the inoculant still generated common detectable abundance changes in at least two of the three locations for several taxonomic groups, some of which have known functionally relevant roles (e.g., *Bacillus, Bradyrhizobium, Flavobacterium, Pedobacter, Sphingomonas*, and *Stenotrophomonas*) affecting yield and other crop/agricultural site features.

The method also included steps for characterizing the co-occurrence and co-exclusion patterns between pairs of OTUs in each sample, as well as steps for estimating ecological emergent properties (i.e. niche specialization, level of competition) which contribute to microbiome functioning. The method thus included architecture for building metacommunities based on all samples and, as an initial filter for bacteria, the method retained OTUs that were detected in at least 30% of the entire dataset, and 90% for fungal communities (e.g., due to the disproportionate number of unique OTUs detected in 16S vs. ITS sequencing, as well as larger variances seen in ITS sequencing). To keep the overall size of the data manageable the method limited the number of selected OTUs to 4,000 with a maximum of 10 million possible significant pairs, and filtered out OTU pairs that were not significantly ($p<0.05$) enriched (co-occurrence) or depleted (co-exclusion). This resulted in metacommunity networks comprising 3,339 nodes for bacteria (19.4% of the total 17,241 bacterial OTUs) and 447 nodes for fungi (26.3% of the total 1,702 fungal OTUs), which on average captured 92.11% of the bacterial abundance and 98.62% of the fungal abundance of the samples. The method then implemented model architecture for exploring the structure of local microbiome communities, based on just the nodes and edges present in each individual sample, aiming to detect changes in network properties that are associated with the application of the bioinoculant at a specific location over time. Specifically, for the co-exclusion and co-occurrence bacterial networks, the method included steps for calculating the modularity (i.e., a measure of the strength of partitioning of a network into modules) and transitivity (i.e., measure of the degree to which nodes in a network cluster together) as well as the proportion of co-exclusions and co-occurrences present in the local network compared to the total number of possible combinations among all OTUs in the sample.

FIGS. 7A and 7B depict outputs of the method capturing the evolution from T0 through T2 of four of the six local network properties studied across locations, for bacterial and fungal populations, respectively. FIG. 7C lists those changes that have been significant (in time—from T0 to T1, and from T0 to T2—in treated vs. untreated blocks. In Grant there was a significant decrease in fungal co-occurrence transitivity and bacterial co-occurrence proportion from T0 to T1 in the treated samples when compared to untreated ones. The model thus captured human intervention in a crop and its effects on altering the structure of microbial communities of the soil, and returned outputs indicating decreased transitivity on the fungal co-occurrence network as a common indicator of these types of alterations. Furthermore, low clustered communities (i.e., those with low transitivity scores) were demonstrated to be associated with highly competitive environments with a high degree of niche specialization, that are among the most relevant properties of an ecosystem when trying to understand its functionality and its response to human interventions and land-use changes. The model also returned outputs indicating a lagged effect (at T2) of the treatment in modifying some network properties of the bacterial communities in both Grant and Sutton. In Grant, the bacterial co-occurrence proportion increases from T0 to T2 (in contrast to the decrease from T0 to T1), and at the same time the transitivity of the bacterial co-occurrence network increases. In Sutton, both the bacterial co-occurrence proportion as well as the bacterial co-exclusion proportion increased from T0 to T2. Thus, when attending to the microbiome structure changes caused by the treatment in Grant and Sutton, which were the locations where treatment had a significant effect over yield, the method highlighted significant treatment-mediated effects over the fungal and bacterial community networks that decreased from T0 to T1, and then increased in T2. Interestingly, and contrary to what was observed in Grant and Sutton, in White Pigeon, the location where treatment didn't have a significant effect over yield, there was an increase in the bacterial co-exclusion modularity from T0 to T1.

In a variation of the example methods described, the method was adapted to further process geophysical metadata/physicochemical data to improve accuracy of predictions of yield (e.g., from ~79% to ~86%). In more detail, the model processed the geolocation of each sample and extracted (e.g., from one or more databases) soil physicochemical data associated with location. In the example, geophysical measurements closest to the sampling point for each sample were averaged; however, in other variations, geophysical metadata/physiochemical data can be acquired at the sampling site (e.g., through direct sampling, through extraction of information from databases, etc.). Processing of geophysical metadata/physicochemical data in addition to microbiome and network data improved predictions of yield significantly, where relative importance factors (based on the Gini index) from variations of the models with and without factoring in geophysical/physicochemical data are shown in the table below:

| Microbiome + networks | | Microbiome + networks + geophysical data | |
|---|---|---|---|
| variable | Importance | variable | Importance |
| Fun_Enriched.Transitivity | 5.12 | Fun_Enriched.Transitivity | 2.17 |
| PC3 | 3.41 | CLAY | 1.85 |
| Fun_Depleted. Coexclusion_proportion | 3.07 | Fun_Depleted. Coexclusion_proportion | 1.70 |
| PC1 | 1.45 | ECEC | 1.50 |
| Location | 1.22 | PH | 1.22 |
| Bac_Depleted. Coexclusion_proportion | 1.08 | PC3 | 1.17 |
| Bac_Enriched. Coexclusion_proportion | 1.08 | TN | 1.03 |
| Fun_Enriched. Modularity | 1.07 | Bac_Enriched. Coexclusion_proportion | 1.01 |
| PC50 | 0.80 | PC1 | 0.97 |
| PC2 | 0.70 | Bac_Depleted. Coexclusion_proportion | 0.93 |

Incorporation of soil physicochemical properties thus improves predictive power of models, and variations of the model can further be adapted to process additional factors (e.g., weather), a reduced number of factors, and/or different combinations of factors to generate further improved predictions of yield.

2.4.4 Crop Feature—Yield Example 2

In a variation of the example methods described, the method was adapted to further process geophysical metadata/physicochemical data to improve accuracy of predictions of yield (e.g., from ~79% to ~86%). In more detail, the model processed the geolocation of each sample and extracted (e.g., from one or more databases) soil physicochemical data associated with location. In the example, geophysical measurements closest to the sampling point for each sample were averaged; however, in other variations, geophysical metadata/physiochemical data can be acquired at the sampling site (e.g., through direct sampling, through extraction of information from databases, etc.). Processing of geophysical metadata/physicochemical data in addition to microbiome and network data improved predictions of yield significantly, where relative importance factors (based on the Gini index) from variations of the models with and without factoring in geophysical/physicochemical data are shown in the table below:

| Microbiome + networks | | Microbiome + networks + geophysical data | |
|---|---|---|---|
| variable | Importance | variable | Importance |
| Fun_Enriched.Transitivity | 5.12 | Fun_Enriched.Transitivity | 2.17 |
| PC3 | 3.41 | CLAY | 1.85 |
| Fun_Depleted. Coexclusion_proportion | 3.07 | Fun_Depleted. Coexclusion_proportion | 1.70 |
| PC1 | 1.45 | ECEC | 1.50 |
| Location | 1.22 | PH | 1.22 |
| Bac_Depleted. Coexclusion_proportion | 1.08 | PC3 | 1.17 |
| Bac_Enriched. Coexclusion_proportion | 1.08 | TN | 1.03 |
| Fun_Enriched.Modularity | 1.07 | Bac_Enriched. Coexclusion_proportion | 1.01 |
| PC50 | 0.80 | PC1 | 0.97 |
| PC2 | 0.70 | Bac_Depleted. Coexclusion_proportion | 0.93 |

Incorporation of soil physicochemical properties thus improves predictive power of models, and variations of the model can further be adapted to process additional factors (e.g., weather), a reduced number of factors, and/or different combinations of factors to generate further improved predictions of yield.

2.4.5 Crop Feature—Crop Nutrient Characteristics Example 1

Variations of the models described were further adapted for returning predictions of a crop's nutrient data (e.g., potato plant petiole nutrient data) based upon a limited number of input features (e.g., soil microbiome-derived features, soil physicochemical features). In more detail with respect to one example, samples were processed from 17 locations across the U.S., and models returned petiole nutrient data indicating plant nutritional statuses, which serves as a proxy for yield and other crop-associated features.

Figure 8A:
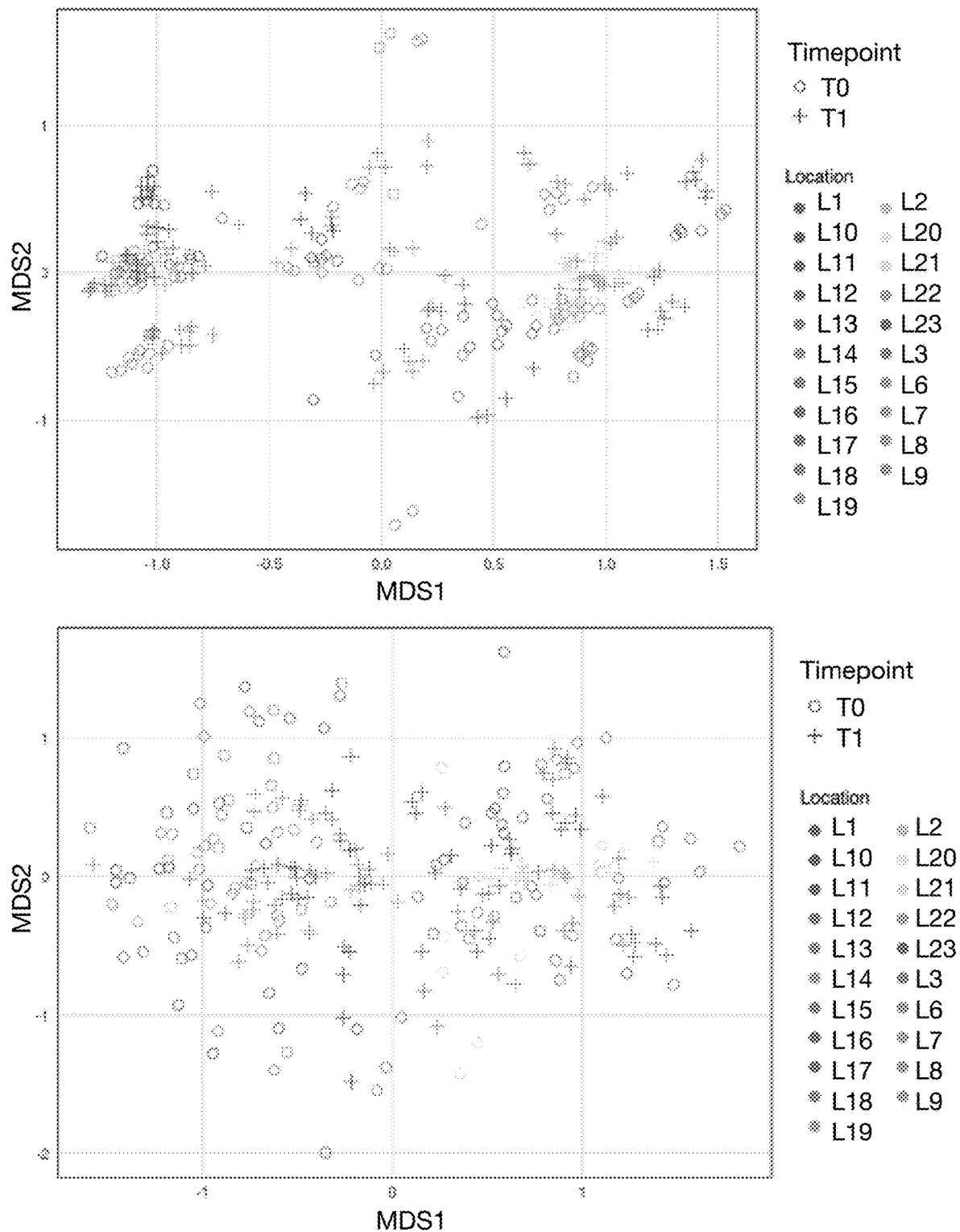
FIGS. 8A-8K depict outputs of stages of a method for evaluating and predicting crop features (e.g., model coefficients, yield, nutritional data).
Figure 8B:
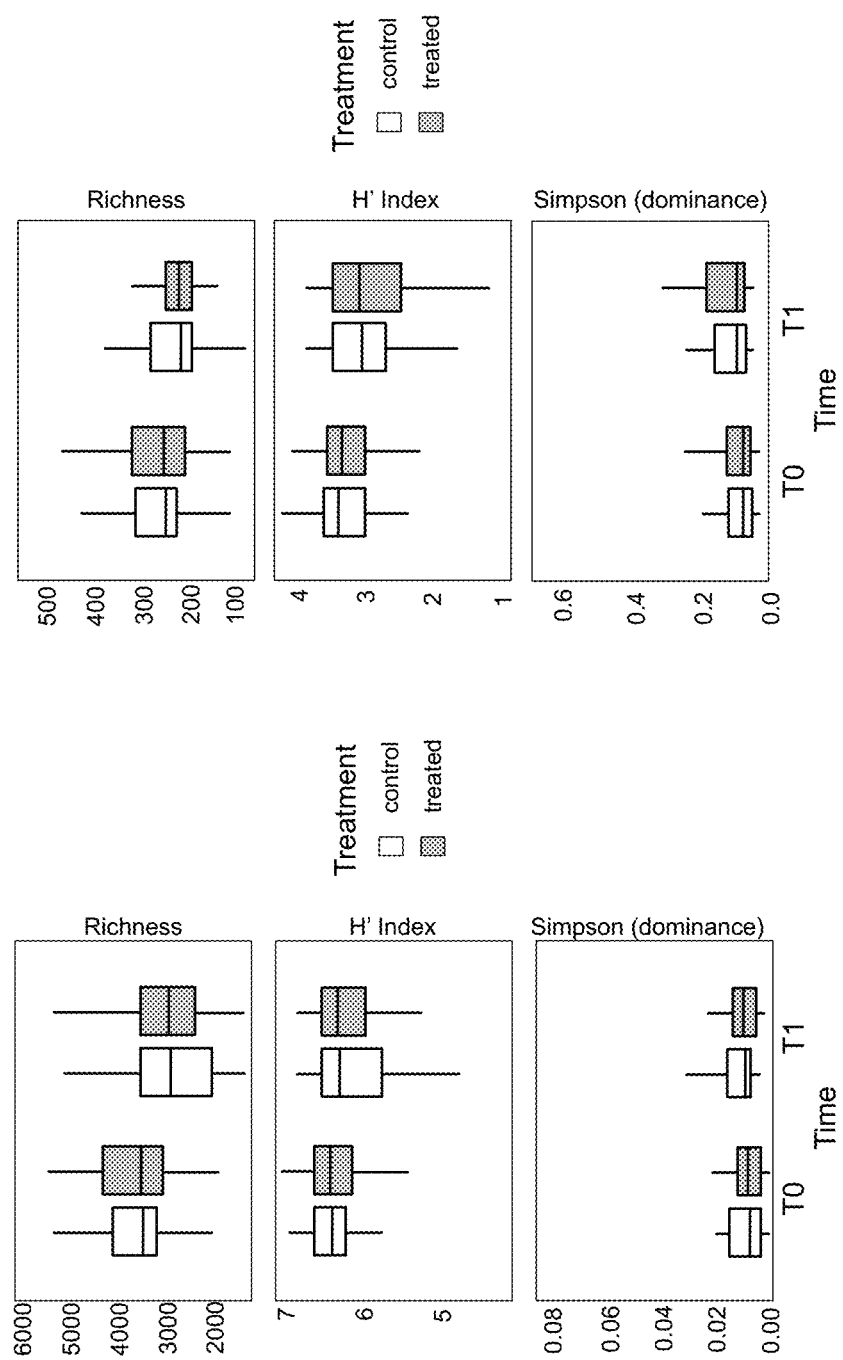
Figure 8C:
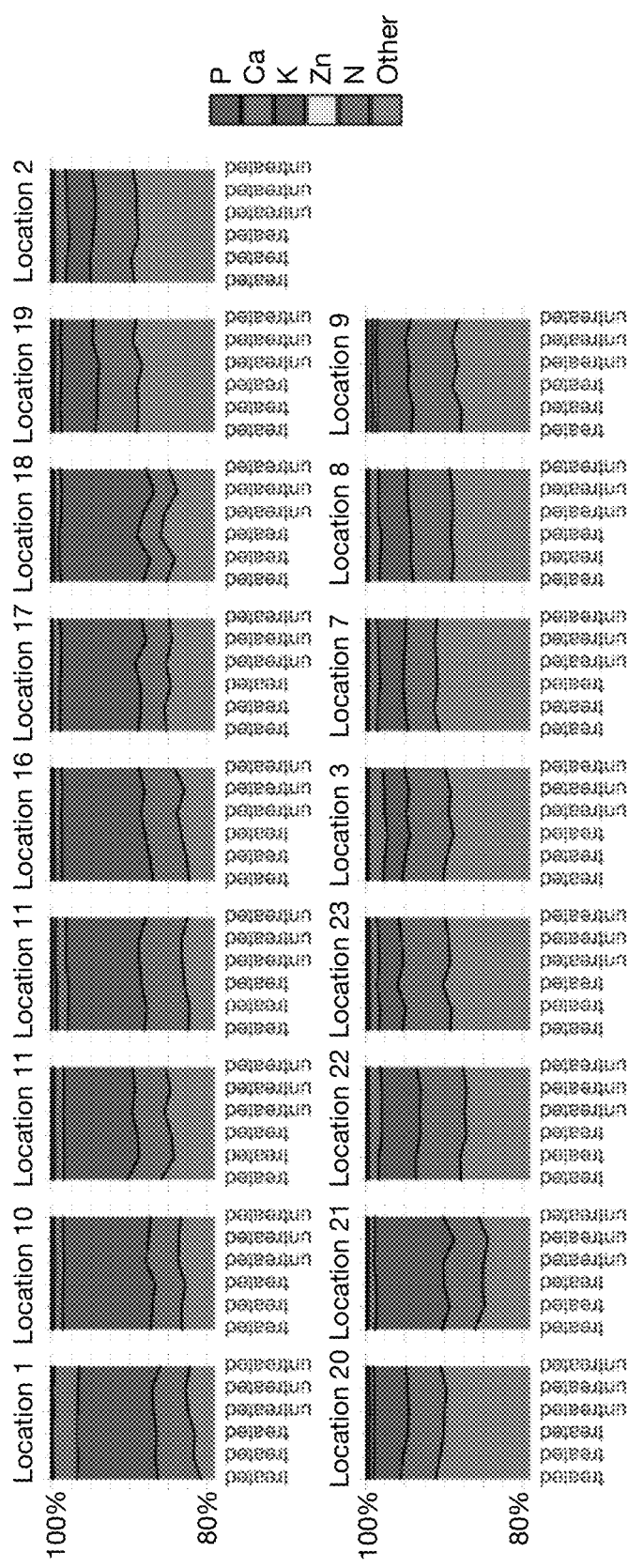
Figure 8D:
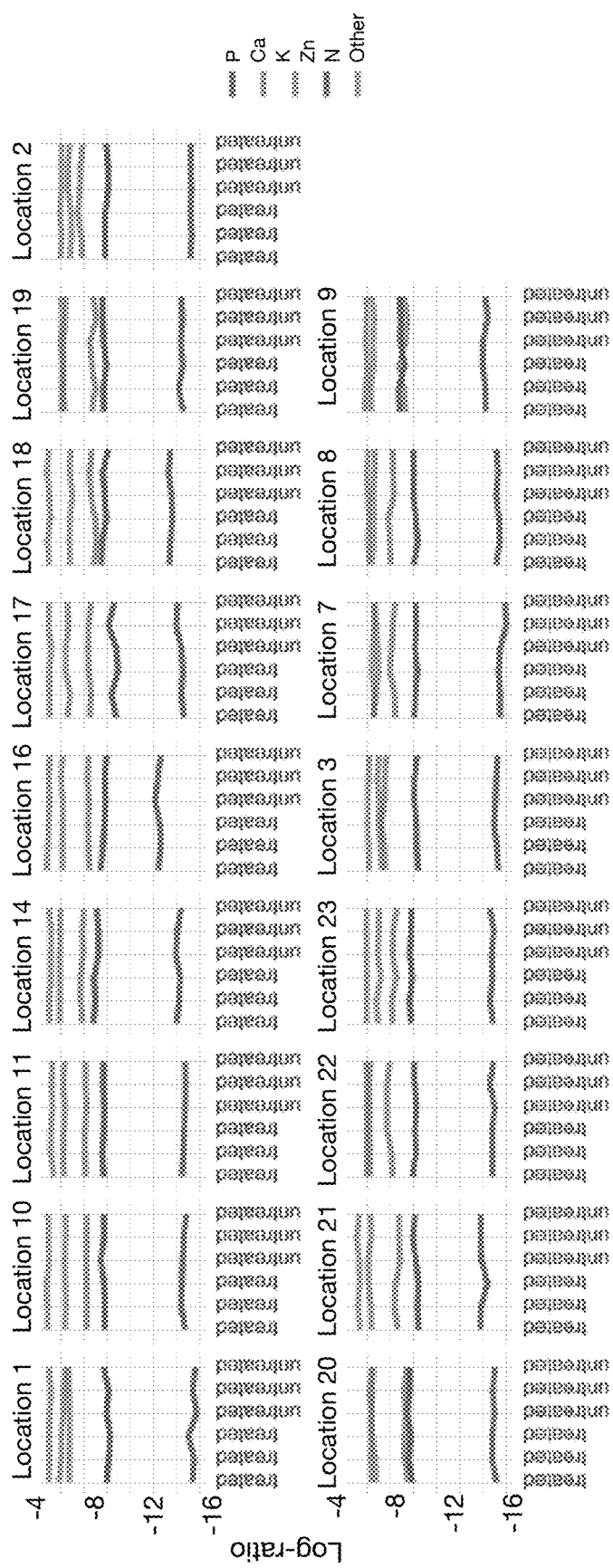

In more detail, as shown in FIG. 8A, the model processed 16S and ITS OTU count data for 17 locations at two time points, which demonstrated strong effects of location on beta diversity. However, alpha diversity (determined from 16S and ITS OTU data) was significantly different across certain locations, but not significantly different with respect to other groupings, as shown in FIG. 8B. Then, as shown in FIG. 8C, the model was structured to return petiole nutrient data for a number (e.g., 102) petiole nutrient data observations from 17 locations, where FIG. 8C depicts part per million (PPM) values of various nutrients (e.g., phosphorus, calcium, potassium, zinc, nitrogen, etc.) converted to percentages for each location. In generating the outputs of FIGURE D, it was observed that treatment effects are subtle (e.g., treatment effects are more appreciable in some locations (e.g. 1 and 16), where treated samples have roughly higher K values). Furthermore, treatment may also be "acting through" other variables, such as network properties. Furthermore, as shown in FIG. 8C, a single component of a percentage composition cannot be changed without affecting additional percentages. The nutrient data variables were then transformed by the model into log-ratio values with a transformation operation that changed the scale of the petiole nutrient concentrations from 0-100% to −inf to +inf (i.e., the whole number range), as shown in FIG. 8D. In the example, the transformation operation processed ratios between concentration/relative abundance values for a particular nutrient and other nutrient values iteratively, with subsequent logarithmic scaling, to adjust the scale in FIG. 8D to [−inf, +inf].

Figure 8E:
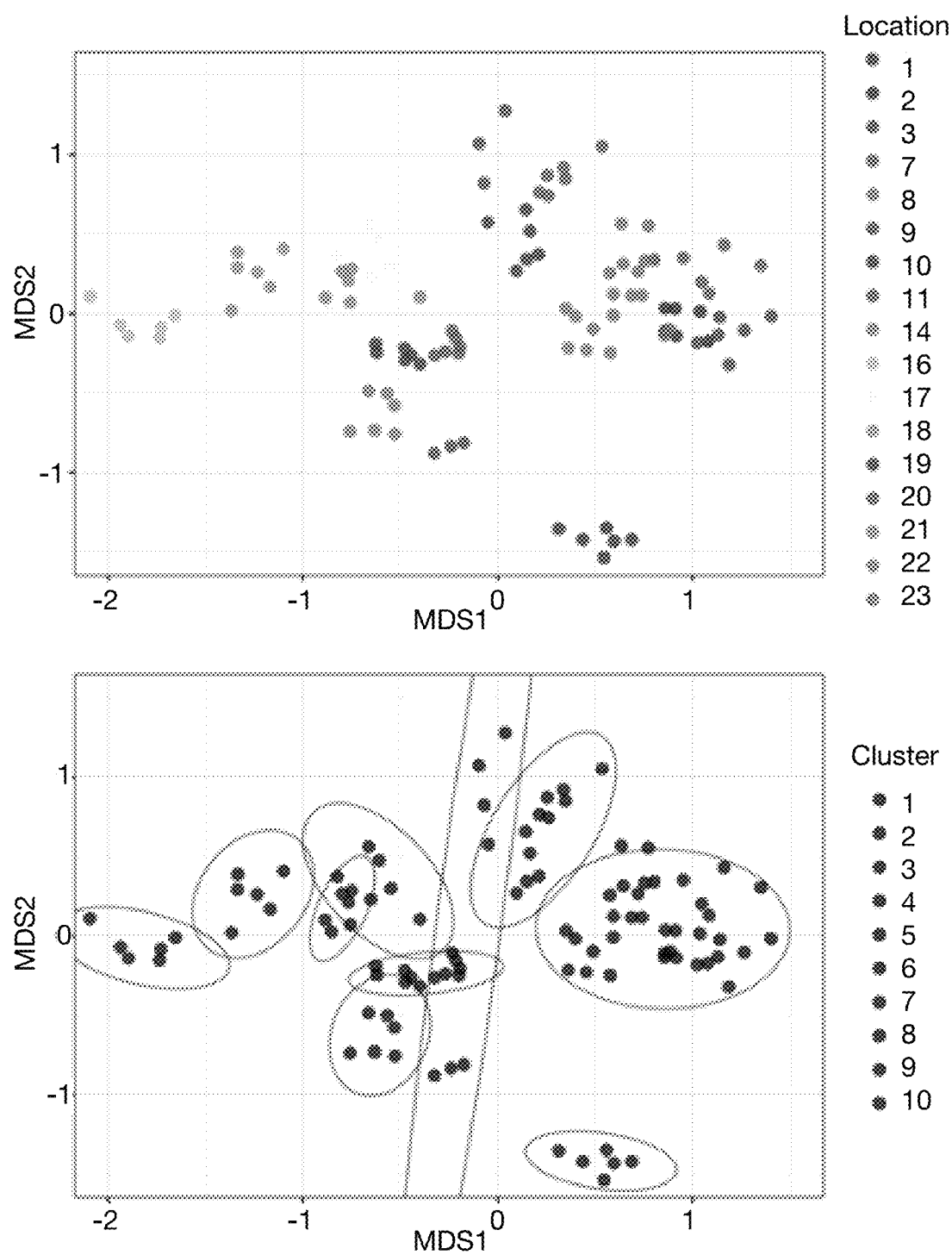
Figure 8F:
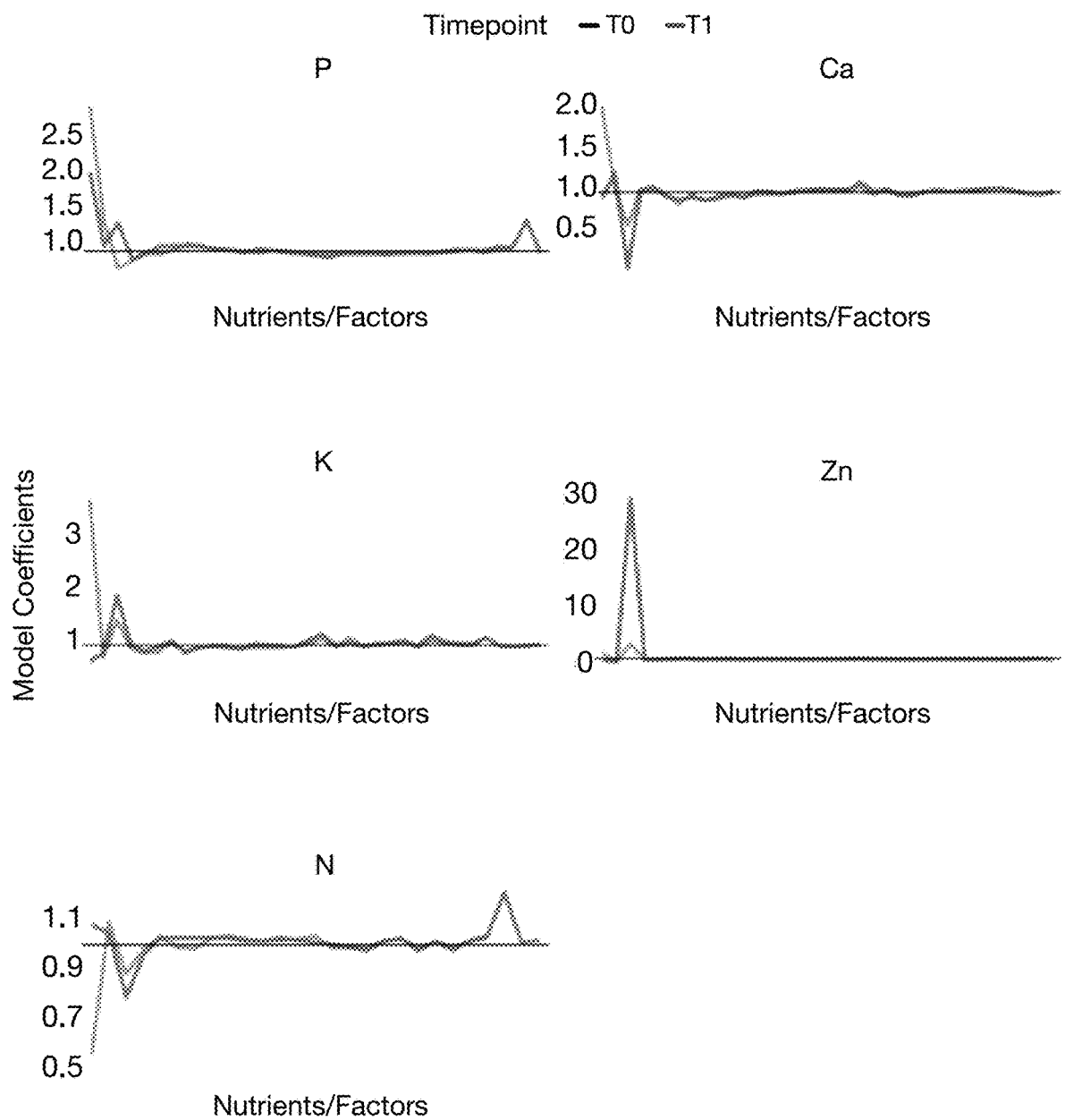

Then, as shown in FIG. 8E, the model performed multidimensional scaling followed by unsupervised clustering of the data to identify clusters of samples, where clusters included samples from single or multiple locations. The model then processed: soil microbiome features (e.g., counts, network properties), texture, and chemical data from multiple time points to generate predictions of petiole nutrient data (and/or data associated with other crop parts), with training of the model based upon a training dataset of 70% of data and a test dataset of 30% of data. The method implemented a multivariate Gaussian LASSO-Ridge regression to model the petiole log-ratios against the input data, where microbiome counts (i.e., 16S and ITS OTU counts) were first CLR-transformed and projected onto a 50-column matrix using classical PCA. Soil chemical and texture data was transformed using a similar procedure as the petiole data. Regression coefficients/fold-changes for multiple time points for each nutrient of interest are shown in FIG. 8F, based on models trained with the training dataset. Nutrients/factors of interest include, but are not limited to: fungi depleted modularity, bacteria enriched modularity, bacteria enriched transitivity, PC15, clay, PC22, PC1, PC7, zinc, PC13, sulfates, PC20, PC25, PC3, potassium, PC17, PC23, PC9, PC10, calcium, PC16, PC8, PC21, PC14, sand, bacterial depleted transitivity, manganese, boron, PC18, PC12, PC6, bacterial depleted modularity, and magnesium (where PC components include compositional components of interest).

In FIG. 8F, the coefficients on the y-axis are fold-changes or "multipliers", where the horizontal line at 1 represents no change, below 1 is a reduction, above one is an increase. In particular, from FIG. 8F, the regression coefficients for T0 and T1 data are similar, but not identical (e.g., for phosphorus, the effect of bacterial enriched transitivity is reversed between timepoints). Furthermore, network properties were demonstrated to have global, but not always similar, effects on petiole data variables, but contributed significantly to predictive power in estimating petiole nutrient characteristics and yield.

Figure 8G:
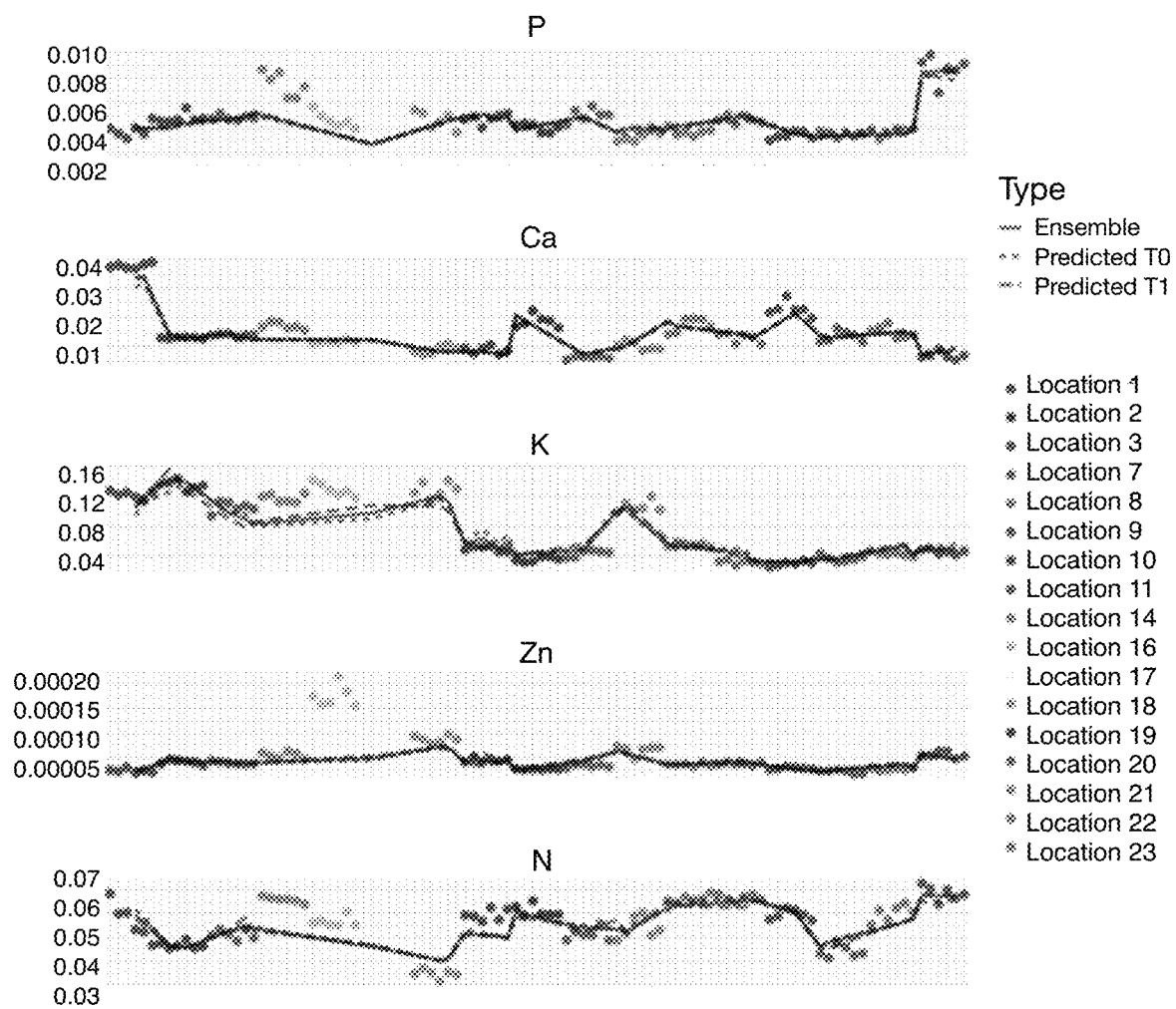

FIG. 8G depicts predictions of coefficients upon processing the test dataset (e.g., with LASSO-Ridge predictions demonstrating 72-92% accuracy in most locations), where the solid line represents ensemble data and the dashed lines represent predicted T0 values and T1 values, respectively. In particular, with respect to processing the test dataset, locations were labeled in the outputs but were not considered as primary factors in generating the predictions. In FIG. 8G, all values on the y-axis are log-ratios (i.e., log 2(element/others)), and the points in FIG. 8G depict the actual values, while lines depict predictions from T0 and T1 respectively. Unexplained outcomes (e.g., in relation to nutrient predictions) can be used for cross-validation of selection of location of sampling in iterations of model development and refinement. The table below depicts percentages of variation explained (i.e., R2 values) by the model for each Petiole nutrient element associated with the test set:

| Petiole element | Ensemble | Predicted T0 | Predicted T1 |
|---|---|---|---|
| P | 87.70% | 88.25% | 87.66% |
| Ca | 92.18% | 89.71% | 92.08% |
| K | 92.37% | 88.07% | 89.68% |
| Zn | 89.25% | 82.45% | 81.41% |
| N | 76.37% | 72.41% | 75.43% |

As such, as shown in FIG. 8G, the microbiome is not only capturing the local microbial "signature", but in conjunction with network properties and soil chemical properties, it is an excellent predictor of petiole chemical composition.

Figure 8H:
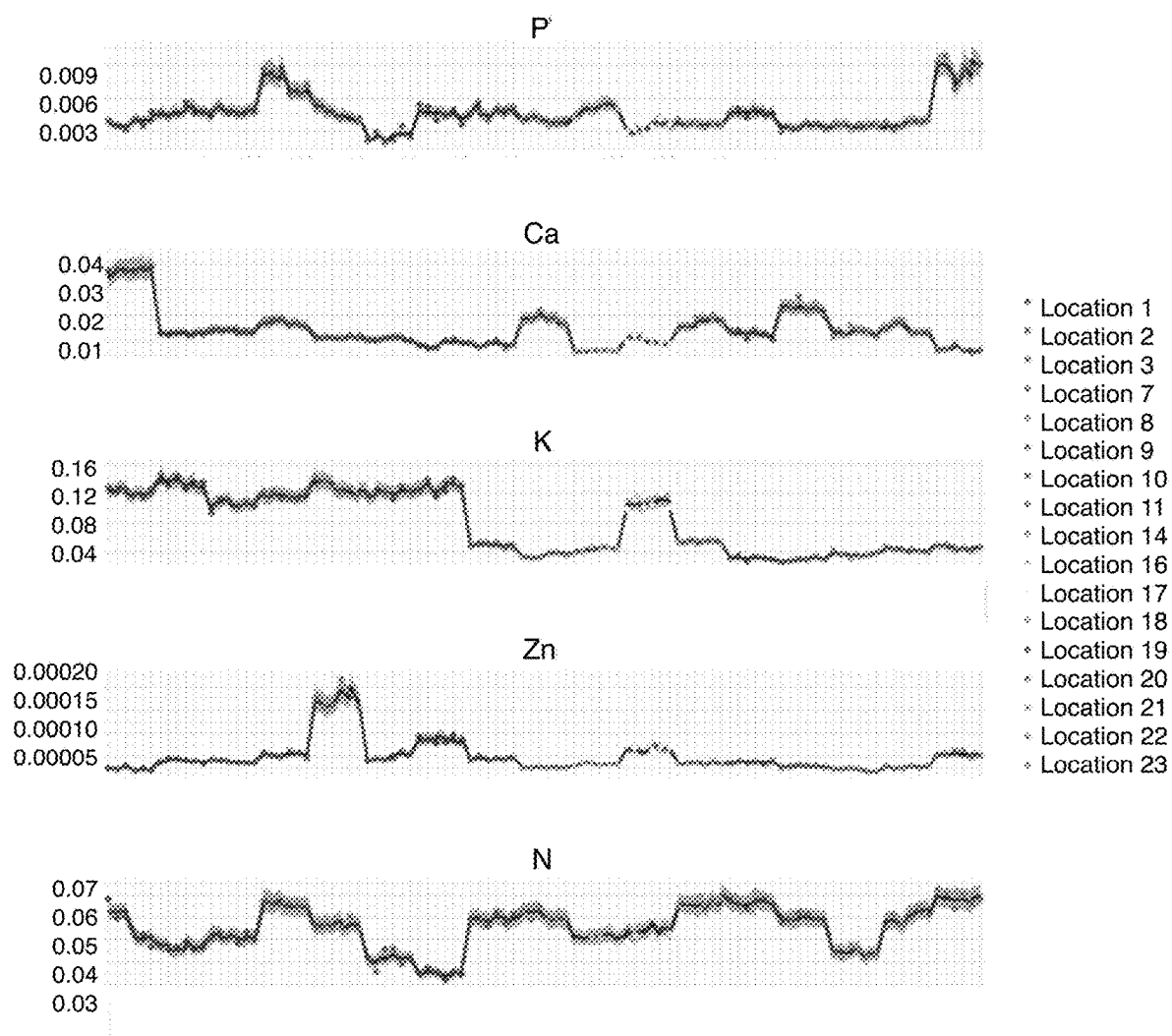

To return insights related to relationships between predictors and predicted variables, the method then included steps for fitting a multi-level Bayesian model (shown in FIG. 8H) with the following architectural aspects configured to ensure a good fit: a baseline was fit for each petiole element for each location, the most important coefficients from the previous regression models (e.g., network properties) were allowed to vary across timepoints, and all network properties and microbiome principal components are allowed to interact with the treatment variable (i.e. the model was configured to assess if the treatment is influencing the coefficients for network properties). Variations of this complex model can implement a subset of the variables or a different set of variables to improve fit. The table below depicts percentages of variation explained (i.e., R2 values) by the model for each Petiole nutrient element associated with the dataset:

| Petiole element | Fitted R2 |
|---|---|
| P | 93.70% |
| Ca | 97.29% |
| K | 99.27% |
| Zn | 97.85% |
| N | 95.56% |

Figure 8I:
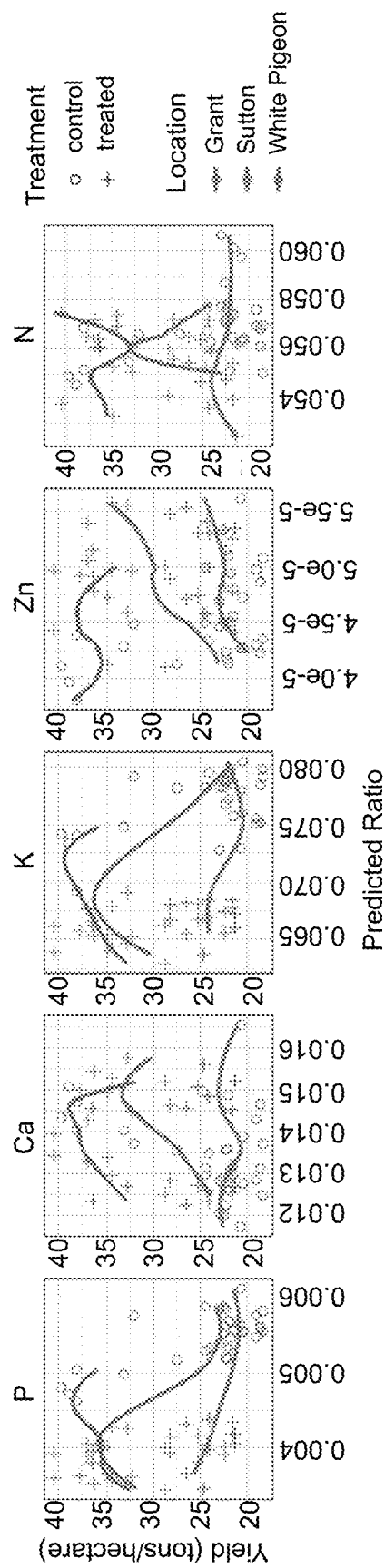
Figure 8J:
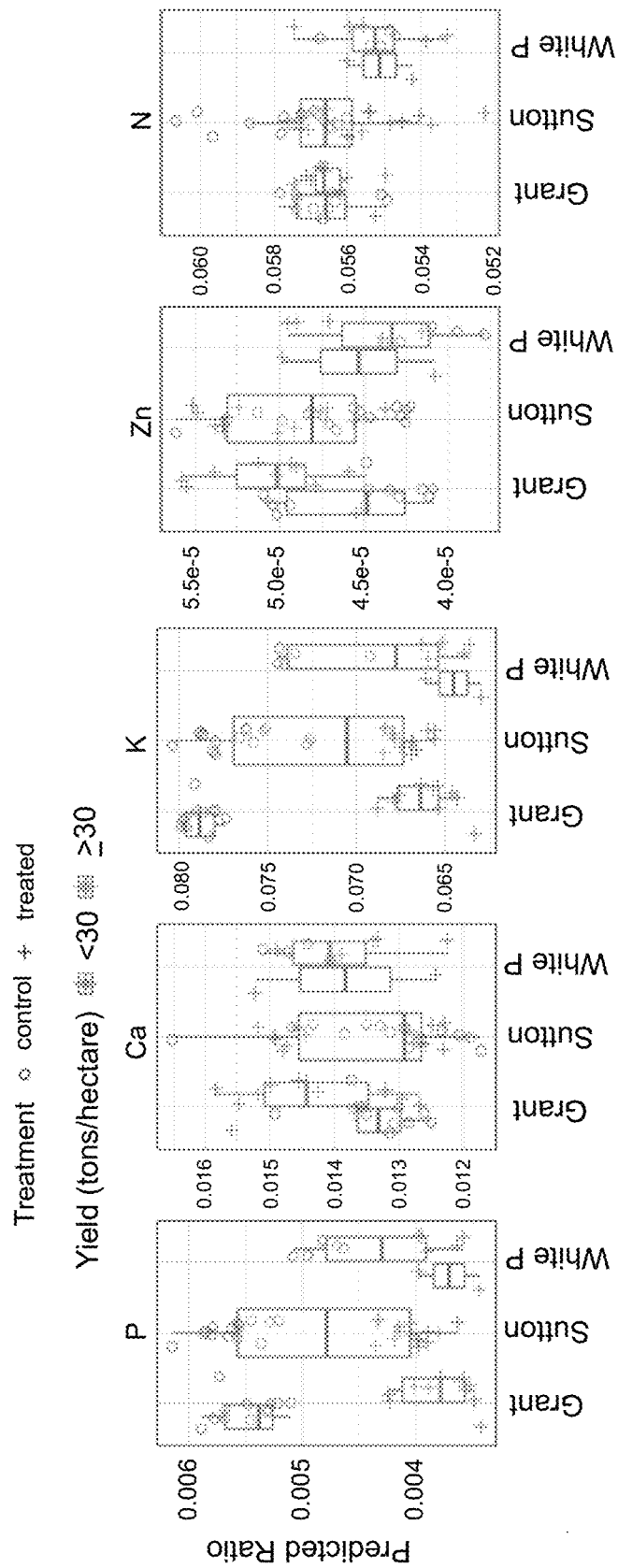

FIG. 8I depicts predictions for petiole nutrients (e.g., P, Ca, K, and Zn) for additional samples, where Potassium and Phosphorous nutrient characteristics were demonstrated to have negative correlations with yield, and Calcium and Zinc were demonstrated to have positive correlations with yield. FIG. 8J depicts predicted ratios of various nutrients, as well as yield predictions, with respect to treatment and control groups at various locations.

Figure 8K:
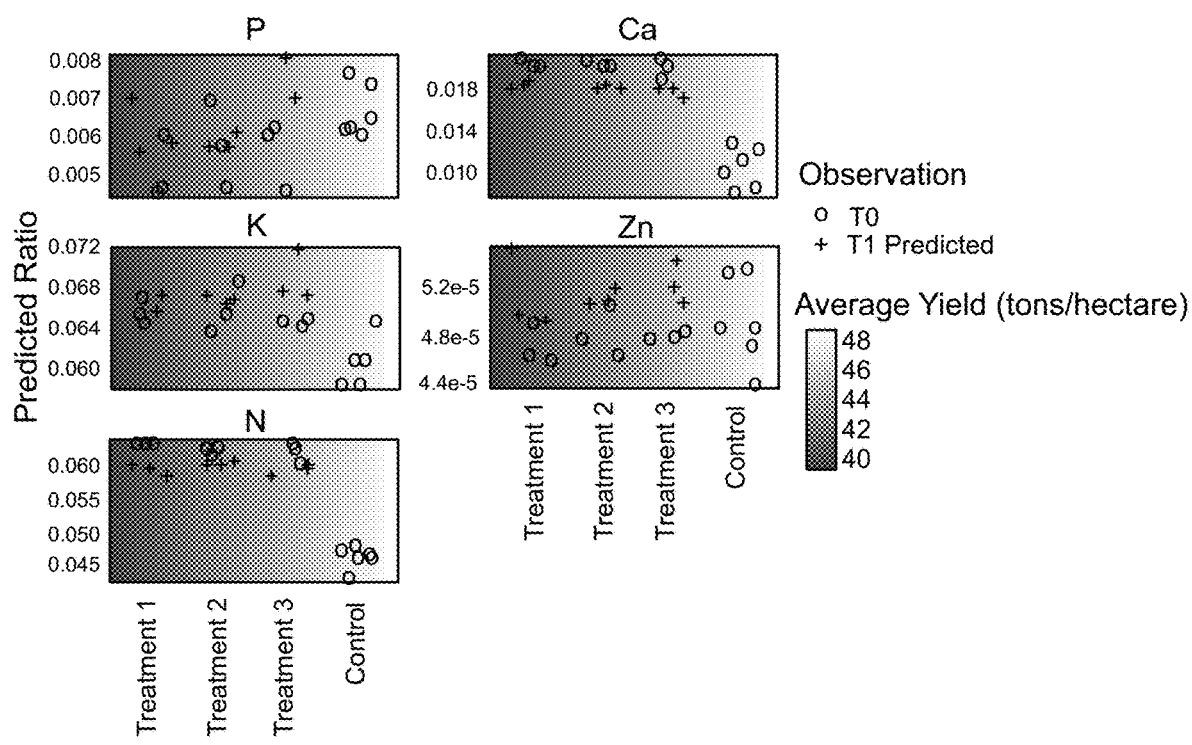

FIG. 8K depicts results of applying three treatments configured for increasing phosphorous solubilization in soil, with returned outputs depicting ratios of various nutrients in response to the treatments, as a proxy for yield (e.g., in terms of average tons/hectare).

Variations of the models described for characterizing nutrient data and/or yield predictions can be structured in another suitable manner (e.g., in relation to model architecture, in relation to input variables processed, etc.). For instance, extensions of described models can be configured to process physicochemical data to return results evaluating the importance of different features in all models, so we can order locations by their "importance" to the predictive power of the models. Such analyses can then be used to rationalize a set of desired or "ideal" soil physicochemical properties and/or weather conditions for which to efficiently evaluate products, other agricultural inputs, and/or other management practices.

2.4.6 Crop Feature—Crop Nutrient Characteristics Example 2

Variations of the models described were further adapted for returning predictions of a crop's nutrient data (e.g., wheat nutrient data) based upon a limited number of input features (e.g., soil microbiome-derived features, soil physicochemical features). Different management conditions (e.g., till versus no-till soils) were also considered in relation to nutrient and yield predictions. The example method for wheat analysis thus includes a comparison between the status of the soil during different timepoints, comparing the evolution of the microbiome of treated (tilled) and untreated (no-till) blocks in several locations. Altogether, this approach limits the impact of the environmental changes in the analysis, and identifies the specific changes caused by the type of soil management in the microbial community.

To characterize both bacterial and fungal microbial communities associated with soil samples, the method includes amplification and sequencing of the 16S rRNA (for prokaryotes) and ITS (for fungi) marker genes (e.g., as described above) for samples (e.g., samples acquired according to variations described above with methods for preventing cross contamination) at multiple geographical locations (e.g., 3 locations) and multiple time points (e.g., 5 time points). The method then includes phylogenetic assignment of each sample based on an average of 300,000 high-quality raw sequencing reads against a taxonomically classified sequence database. The method also includes computation of functional and ecological indexes according to embodiments, variations, and examples of methods described above, with soil physical/chemical properties evaluated (e.g., using Waypoint Analytical's Mehlich 3 Extraction) with a suitable buffer (e.g., pH, buffer pH, P, K, Mg, Ca, organic matter, CEC, % cation saturations) and B, S, Fe, Mn, Cu, Zn and Na. The method further includes steps for providing individual report per sample as well a guide for evaluating results and implementing recommendations. Once physicochemical properties as well as taxonomic, functional and ecological indexes are obtained for all samples, the method can be used to evaluate potential relationship between the soil's initial characteristics, the microbiome, and the nutritional quality of the wheat. As such, similar to methods described above, the method here can be adapted to use classic statistical, Bayesian, and/or machine learning models based on the physicochemical and biological properties of soil to predict or correlate it to nutritional quality of a wheat species (e.g., *Triticum aestivum* L).

Variations of the methods described can further be configured to evaluate the carbon sequestration capabilities at an agricultural site (e.g., using methods adapted from those above in relation to yield and nutrient characterizations and predictions). As such, the adapted methods can be used to benefit land managers in relation to obtaining soil carbon credits from their lands, predicting shelf life of crops based on the soil microbiome, and/or in relation to other suitable benefits.

2.5 Methods—Insights and Interventions

Step S150 recites: executing an action for producing a desired outcome in relation to the agriculture site, with respect to a specific soil type and a specific crop, based upon the analysis. Step S150 functions to process outputs of prior steps in order to generate insights and/or execute actions that can improve productivity, correct issues, and/or increase sustainability of practices at the agriculture site(s) being assessed. In particular, agricultural inputs and management practices can have inconsistent field performance with uninformed application, where, in relation to some inputs, different strains and species can have different functional performance under specific environmental and ecological conditions. As such, Step S150 can provide agricultural inputs and implement management practices in an informed manner that is targeted to specific crops, soil types, and/or environmental conditions.

In variations, executing the action can include generating digital objects encoding instructions for controlling apparatus associated with an operator managing the agriculture site. In variations, executed actions can include or be associated with one or more of: maintaining a status of an agriculture site by providing guidance for maintaining current management statuses and/or products used; responding to an issue detected at the agriculture site(s) being assessed (e.g., in relation to pathogen presence or increased abundance of a detrimental microorganism, in relation to decreased abundance of a beneficial microorganism, in relation to correcting a perturbation, in relation to adjusting application of a product at the agriculture site, implementing protective measures against environmental effects, etc.); responding to or otherwise correcting other undesired statuses at one or more agriculture sites being monitored; providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions.

In generating recommended actions, step S150 can include returning notifications or other information derived from the analyses and other outputs of step S140 in a visual format, in an audio format, in a haptic format, and/or in any other suitable observable format, to a manager, operator, and/or other entity associated with the agriculture site(s) being assessed. As such, variations of Block S150 can include generating digital objects (e.g., in visual data formats, in audio data formats, in haptic data formats, encoding information) or instructions for generating digital objects, in communication with client devices (e.g., mobile devices or other devices that are associated with a manager, operator, and/or other entity associated with the agriculture site(s)), where the client devices include visual output components (e.g., a display), audio output components (e.g., speaker), haptic output components (e.g., vibrators), and/or any other suitable components. Client devices can also include input components (e.g., keypads, touch displays, microphones, joysticks, mice, etc.) such that the managers, operators, or other entities associated with the agriculture site(s) can communicate inputs (e.g., commands) related to the generated analyses.

Additionally or alternatively, generating recommended actions can include generating control instructions for apparatus (e.g., machinery, robotic apparatus configured to traverse an agricultural site, other apparatus) configured to execute computer-readable instructions for management of the agriculture site(s).

In variations, control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery or pesticide delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s). Additionally or alternatively, step S150 can include generation of control instructions for automated vehicle platforms associated with controlling vehicles associated with the agriculture site(s), with respect to surveying, management, and/or other operation modes.

In examples, instructions for controlling operation modes of watering subsystems (e.g., in relation to water distribution through conduits and/or sprinklers to the agriculture site(s)) can be automatically executed in response to detected states of undesired watering levels based upon model outputs from other steps of the method. As such, controlling operation modes can include transitioning the watering subsystems between various states of flow, on-off states, etc. Control can be modulated in relation to constraints associated with water usage (e.g., times of drought, in relation to water usage incentives, etc.).

In examples, instructions for controlling operation modes of product delivery subsystems (e.g., delivery subsystems in communication with watering subsystems through fluidic components, valves, etc.) can be automatically executed in response to detected states of undesired supplement levels based upon model outputs from other steps of the method. As such, controlling operation modes can include transitioning the delivery subsystems between various states of product dosage, flow rates, on-off states, etc.

In examples, instructions for controlling operation modes of robotic crop handling subsystems (e.g., in relation to removal of pathogen-affected crop portions), robotic crop picking subsystems (e.g., in relation to automated harvesting at optimal time periods in relation to improving production, in relation to efficiency of new production generation post-harvesting, in relation to minimization of wasted product, etc.), robotic nutrient delivery or pesticide delivery subsystems (e.g., in relation to initiating delivery, in relation to stopping delivery, in relation to adjusting frequency of delivery, in relation to adjusting delivery dosages, etc.), and/or other robotic subsystems can be automatically executed in response to detected states of harvesting time, pathogen detection, nutrient states, pest presence, and/or other factors based upon model outputs from other steps of the method. As such, controlling operation modes can include transitioning the robotic subsystems between various states of actuation.

In examples, instructions for controlling operation modes of greenhouse subsystems, temperature control subsystems (e.g., in relation to modes for controlling environmental temperature of the agriculture site, etc.), light control subsystems (e.g., in relation to modes for controlling environmental light of the agriculture site, in relation to transitioning between on and off states, in relation to light spectrum delivered, etc.), gas environment subsystems (e.g., in relation to modes for controlling environmental gas composition of the agriculture site, etc.), humidity control subsystems (e.g., in relation to modes for controlling environmental humidity levels of the agriculture site, etc.), pressure control subsystems (e.g., in relation to modes for controlling environmental pressure of the agriculture site, etc.), and/or other environmental control subsystems can be automatically executed in response to detected states of environmental conditions suited to or unsuited for desired outcomes, and/or other factors based upon model outputs from other steps of the method. As such, controlling operation modes can include transitioning the environmental control subsystems between various states of temperature control, light control, gas control, humidity control, pressure control, and/or other environmental control. Control can be modulated in relation to constraints associated with power usage (e.g., times of peak demand, in relation to demand incentives, etc.).

Additionally or alternatively, step S150 can include generation of control instructions for automated vehicle platforms associated with controlling vehicles associated with the agriculture site(s), with respect to surveying, management, and/or other operation modes.

Step S150 can include or be associated with executing the recommended action S151 through electronic communication with one or more subsystems described above, which functions to automatically execute recommended actions in order to reduce operator workload in relation to agriculture site management. Executed actions can include or be associated with one or more of: maintaining a status of an agriculture site by providing guidance for maintaining current management statuses and/or products used; responding to an issue detected at the agriculture site(s) being assessed (e.g., in relation to pathogen presence, in relation to detrimental microorganism presence, in relation to correcting a perturbation, in relation to adjusting application of a product at the agriculture site, implementing protective measures against environmental effects, etc.); responding to or otherwise correcting other undesired statuses at one or more agriculture sites being monitored; maintaining or improving desired statuses at one or more agriculture sites being monitored (e.g., in relation to biocontrol microorganism presence, in relation to stress tolerance microorganism presence, in relation to plant growth promoter microorganism presence, in relation to nutrient metabolizing microorganism presence, etc.); providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions, as described above in embodiments, variations, and examples of agriculture site management control and notification/report delivery. Embodiments, variations, and examples of actions are further described in U.S. application Ser. No. 17/119,972 filed 11 Dec. 2020, incorporated by reference above.

2.5.1 Agricultural Input Examples

In examples, agricultural inputs can include substances, microorganisms, or mixtures thereof (e.g., plant biostimulants) configured to promote plant health and quality and recycling crop residues with low environmental impact. Such inputs can include biofertilizers, biostimulants, biocontrol agents, agents for hormone production, agents configured to promote stress adaptation, nutrients, and/or other inputs. Bioinoculants based on microorganisms, in particular, can include functional plant growth promoter species having a direct impact on plant health and yield. In examples, such biostimulants can function by: improving plant growth, increasing root hairs development in a phytohormone-mediated process using an Azospirillum brasilense strain; by increasing the tolerance to abiotic stresses through the action of an ACC deaminase produced by a *Burkholderia unamae* strain; by increasing plant growth by enhanced nutrient (P) acquisition (e.g., in cucumber and tomato plants) using a *Bacillus* sp. strain; by enhancing nodule formation by a two species consortia of *Pseudomonas putida* plus *Rhizobioum* sp. (e.g., in beans); by improving grain yield (e.g., in rice) by increasing panicle number through the use of an Azospirillum amazonense strain; by improving nutrient (e.g., phosphorous) solubilization; and/ or by another suitable method.

Additionally or alternatively, agricultural inputs can include microbial strains that have indirect effect in soil and plant health, as tools for in situ microbiome engineering, promoting the development of other beneficial microbial species, improving the resistance of the microbiome to the invasion of plant pathogens (e.g., as in *B. amyloliquefaciens* QST713—a strain isolated from the soil of a Californian organic peach orchard with a demonstrated effective broad-spectrum bactericide and fungicide activity), having another function in affecting composition and structure of native communities (e.g., as in allochthonous strains), and thus reducing the abundance of pathogenic species, thereby increasing the resistance of the plant against diseases.

In the specific example provided above, *B. amyloliquefaciens* QST713-based biostimulants can be used to reduce the transitivity of the co-occurrence fungal network of the rhizosphere and bulk soil where it is applied through its biofungicide activity, but in a reversible manner, thereby improving yield in the short term, but maintaining crop health in the long term. That is, effects of *B. amyloliquefaciens* QST713-based biostimulants can operate in a transient, reversible, and/or non-permanent manner (e.g., the fungal communities return to their original stage post-harvest), thereby improving yield significantly but not having a permanent or adverse effect upon crop or site health.

2.5.2 Management Practice Examples

In examples, management practices can include one or more of: implementation of cover crops, conservation tillage, irrigation efficiency-associated methods, contour farming, implementation of waste storage structures for animal waste, critical area planting, crop residue management practices, crop rotation, diversion, forest harvest management, use of grade stabilization structures, application of grassed waterways, use of high tunnels, implementation of integrated pest management, implementation of silvopasture, implementation of cover grazing, implementation of no-till farming, implementation of nutrient management plans, roof runoff management, implementation of rotational grazing, implementation of vegetative filter strips to filter runoff and prevent contaminants from entering water sources, implementation of field borders, implementation of lined waterways, implementation of riparian buffers, and/or other management practices.

As described above, management practices can be categorized or specific to one of: conventional management practices, organic management practices, and biodynamic management practices, and other suitable types of management practices. As such, executing the action can include implementing one or more of: a conventional management practice, an organic management practice, and a biodynamic management practice at the agriculture site.

2.5.3 Practical Implementation Examples

Based on embodiments, variations, and examples of methods and models (e.g., trained models) described above, as shown in FIGS. 8A and 8B, step S150 can include receiving a dataset associated with one or more of a crop type and an agricultural site (e.g., geolocation of the agricultural site) under evaluation S151*a* and/or receiving a sample from the agriculture site under evaluation S151*b*; processing at least one of the dataset and the sample with an embodiment, variation, or example of the model(s) described above S152; returning a prediction of a crop-associated feature from the model(s) S153; and based upon the prediction, recommending or executing implementation of at least one agricultural input or management practice at the agricultural site under evaluation S154.

In variations, S154 can extend to evaluating a set of agricultural inputs and/or management practices in parallel within subportions of the agricultural site under evaluation by applying the set of agricultural inputs and/or management practices in parallel at a set of subportions of the agricultural site S155; processing samples acquired from the set of subportions S156; and returning outputs characterizing crop-associated features and/or characteristics of the set of subportions, at a set of time points, in response to the set of agricultural inputs and/or management practices S157, thereby characterizing effectiveness of each of the set of agricultural inputs and/or management practices.

In one variation of step S151*a*, an entity associated with the crop type and/or agricultural site under evaluation can be prompted to provide information pertaining to a geolocation of the agricultural site and/or the crop type the entity is interested in cultivating. Then, upon processing the information (e.g., using variations of models described above, by extracting physicochemical data and/or weather data from databases based upon the geolocation, etc.) according to step S152, the method can return a prediction of the crop-associated feature (e.g., yield prediction, nutrient prediction, health prediction, etc.) for the crop type and/or agricultural site under evaluation according to step S153, and execute an action (e.g., providing product recommendations, implementing management practices, applying products targeted to the condition of the crop/agricultural site, etc.) for achieving desired outcomes according to step S154. Examples of desired outcomes can include one or more of: an increase in yield, protection of one or more crop types from disease, improving nutrition state or content of crop types, increasing the shelf life of crop types, achieving agricultural site states that facilitate selling of soil carbon credits, and other outcomes.

In one variation of step S151b, an entity associated with the crop type and/or agricultural site under evaluation can be prompted to provide information pertaining to a geolocation of the agricultural site and/or the crop type the entity is interested in cultivating, along with a sample (e.g., derived from soil, derived from a crop portion, derived from material produced from a crop, etc.). Then, upon processing the information (e.g., using variations of models described above, by generating microbiome composition and structure-associated features, by extracting physicochemical data and/or weather data from the sample(s) directly, etc.) according to step S152, the method can return a prediction of the crop-associated feature (e.g., yield prediction, nutrient prediction, health prediction, etc.) as well as information pertaining to the sample and/or agricultural site (e.g., providing physicochemical data for the agricultural site) according to step S153, and execute an action (e.g., providing product recommendations, implementing management practices, applying products targeted to the condition of the crop/agricultural site, etc.) for achieving desired outcomes according to step S154. Examples of desired outcomes can include one or more of: an increase in yield, protection of one or more crop types from disease, improving nutrition state or content of crop types, increasing the shelf life of crop types, achieving agricultural site states that facilitate selling of soil carbon credits, and other outcomes.

In relation to evaluating agricultural inputs and/or management practices in parallel according to variations of steps S155-S157, variations of the method can include steps for performing field trials of multiple agricultural inputs (e.g., biostimulants, biofertilizers, crop protection products, etc.) at one or more geolocations. at one or more time points, and/or in association with one or more crop types (e.g., genotypes, cultivars). Data from evaluation of sets of agricultural inputs and/or management practices can be used to generate additional data (e.g., training data, test data) for refining models described above.

In one example, the method can be used to evaluate agricultural inputs comprising phosphorus solubilizers, where processing of samples and/or other data from agricultural sites where the phosphorous solubilizers were applied produced outputs indicative of effectiveness of the phosphorous solubilizers. Evaluation can be based upon microbiome composition, functional and structural features, as well as crop symptoms determined directly. In the example, each product being examined in parallel was evaluated for effects on crop health (e.g., in relation to brown spot, in relation to black pit, in relation to charcoal rot, in relation to early blight, in relation to *Fusarium* dry rot, in relation to *Fusarium* wilt, in relation to gray mold, in relation to late blight, in relation to pink rot, in relation to *Pleospora herbarum*, in relation to silver scurf, in relation to *Verticillium* wilt, etc.); in relation to hormone production (e.g., in relation to auxin production, in relation to cytokinin production, in relation to gibberellin production, etc.); in relation to stress adaptation (e.g., in relation to exopolysaccharide production, in relation to ACC deaminase abundance, in relation to heavy metal solubilization, in relation to salicylic acid production, in relation to salt tolerance, in relation to abscisic acid production, in relation to sidero-phore production, etc.); in relation to biocontrol behavior (e.g, in relation to fungicide agents, in relation to insecticide agents, in relation to nematicide agents, in relation to bactericide agents, etc.); in relation to nutritional pathways associated with major compounds associated with carbon pathways (e.g., carbon fixation, aerobic respiration, fermentation, methanogenesis, organic matter release, etc.); in relation to nutrition associated with major compounds associated with nitrogen pathways (e.g., inorganic nitrogen release, inorganic nitrogen consumption, inorganic nitrogen cycle health, etc.); in relation to nutrition associated with major compounds associated with phosphorous pathways (e.g., inorganic phosphorus solubilization, inorganic phosphorous consumption, organic phosphorous assimilation, etc.); in relation to nutrition associated with major compounds associated with potassium pathways (e.g., potassium solubilization, potassium consumption, etc.); in relation to nutrition associated with major compounds associated with other pathways; in relation to other micronutrient factors (e.g., iron assimilation, zinc transport equilibrium, manganese transport equilibrium, sulfur cycle equilibrium, calcium transport, copper export, magnesium transport, chlorine transport, etc.); and/or other factors.

Variations of the methods described also evaluated soil microbiome agronomic indices (e.g., as described above) that improved the most upon application of each product, in relation to metrics and categories of evaluation described above.

Variations of the methods can, however, be implemented in another suitable manner or drive other suitable outcomes.

3. System

As shown in FIG. 9, a system 200 for characterization and improvement of an agricultural site includes: one or more sample reception subsystems 210; one or more sample processing subsystems 220 in communication with the sample reception subsystems 210; a computing platform 230 comprising one or more processing subsystems comprising non-transitory computer-readable medium comprising instructions stored thereon, that when executed by the processing subsystems perform one or more steps of methods described above; and one or more action execution subsystems 240 configured to execute actions informed by processes of the computing platform 230. In variations, the action execution subsystems 240 can be configured to execute control instructions generated by the computing platform 230, where control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s).

Embodiments of the system 200 are configured to perform one or more portions of methods described above; however, variations of the system 200 can be configured to perform other suitable methods.

4. Conclusions

The invention(s) decipher different ecological strategies that bacterial, fungal, and/or other organism communities adopt in face of different levels of farming intensification and product use, and explore how these may impact soil health in terms of external factors and plant pathogens. In applications, outputs of the invention(s) can guide interventions and/or other practices to improve agriculture sites, as observed community assembly strategies. In examples, a collaborative well-mixed habitat in soils under biodynamic management with potentially higher resistance towards, at least, pathogen loads, or a more divided habitat, with fungi belonging to more niches but with lower reaction range to pathogen loads in soils under conventional management. Under this framework, the inventions have practical applications with relevance for agriculture sustainability, and with respect to interventions that can be designed to drive a better future for agro-ecosystems. For instance, evaluating how emergent properties change during time-series, may give clear indications about the resistance and resilience of fungal communities, or shed light into the dynamics of soils under different anthropogenic disturbances. For now, the defined ecological emergent properties may be used as biomarkers to measure the effect of farming practices or temperature change consequences in the health status of soils. Given the key role that microorganisms play in agrifood systems in general, and in crop yield in particular, these findings are useful for establishing monitoring programs of crop-associated microbial diversity, supporting the work of alliances such as the soil health institute the U.S. department of agriculture, or the global initiative of crop microbiome and sustainable agriculture, while promoting soil healthiness through agriculture sustainable strategies.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A method for producing a desired outcome at an agriculture site, the method comprising:
   receiving a set of samples associated with the agriculture site;
   generating a set of microbiome-associated features and extracting soil physicochemical data upon processing the set of samples with a set of sample processing operations comprising a target amplification operation, a target sequencing operation, and a library preparation operation,
   wherein generating the set of microbiome-associated features comprises generating a feature characterizing a transitivity of a co-occurrence network represented in the set of samples, wherein the transitivity characterizes a degree to which nodes in the co-occurrence network are clustered;
   returning an analysis characterizing a set of crop-associated features based upon the set of microbiome-associated features; and
   executing an action for producing a desired outcome in relation to the agriculture site, with respect to a specific soil type and a specific crop, wherein executing the action comprises applying a biostimulant configured to reduce transitivity of the co-occurrence network of the agriculture site, based upon the analysis.

2. The method of claim 1, wherein the set of samples comprise at least one of: a soil sample, a root sample, a foliage sample, a liquid sample, and a crop-derived sample.

3. The method of claim 1, wherein the co-occurrence network is a fungal co-occurrence network, and wherein applying the biostimulant comprises applying a *B. amyloliquefaciens* QST713-based biostimulant configured to improve yield and maintain health of the specific crop.

4. The method of claim 1, wherein the set of transformation operations further comprises tagging sequence data of the sample dataset with: contextual data comprising geographic location information, meteorological metadata, climatic information, and management practice information; and a set of metacommunity descriptors corresponding to a set of communities within a same habitat associated with the agriculture site.

5. The method of claim 1, wherein performing the set of transformation operations comprises generating a first grouping of positive pairs of organisms and a second grouping of negative pairs of organisms represented in the sample dataset, and generating a network property dataset upon transforming the first grouping of positive pairs of organisms and second grouping of negative pairs of organisms into a set of aggregate matrices representing co-inclusion and co-exclusion of organisms across a metacommunity represented in the sample dataset.

6. The method of claim 1, wherein receiving the set of sample comprises receiving the set of samples across a set of time points, and wherein returning the analysis comprises returning characterizations of evolving phenological stage dynamics within organism populations at the agriculture site, based upon alpha diversity and beta diversity patterns.

7. The method of claim 6, wherein returning characterizations of evolving phenological stage dynamics comprises returning characterizations of operational taxonomic unit (OTU) and amplicon sequence variant (ASV) richness and diversity across the set of time points.

8. The method of claim 1, wherein returning the analysis comprises returning a set of predictors of yield of crops at the agriculture site.

9. The method of claim 8, wherein returning the set of predictors of yield comprises returning values of fungal co-occurrence transitivity, fungal co-exclusion proportion, and fungal composition associated with the agriculture site.

10. The method of claim 1, wherein returning the analysis characterizing the set of crop-associated features comprises returning predictions of nutrient data associated with a portion of a crop at the agriculture site.

11. The method of claim 1, wherein the set of microbiome-associated features is derived from combinations of p-hypergeometric (PH) network properties and Bayesian factor (BF) network properties.

12. The method of claim 1, wherein returning the analysis comprises generating a set of outputs characterizing agriculture site statuses associated with nutritional composition features of soil at the agriculture site.

13. The method of claim 1, wherein returning the analysis comprises generating a set of outputs characterizing responses to a set of perturbations associated with the agriculture site.

14. The method of claim 1, wherein the set of crop-associated features comprise: yield characteristics; crop health and disease states; crop age characteristics comprising lifespan, cycles of productivity, vegetative growth state; and crop shelf life.

15. The method of claim 1, wherein executing the action comprises generating digital objects encoding information derived from the analysis and providing information derived from the analysis to an operator associated with the agriculture site.

16. The method of claim 1, wherein executing the action comprises generating control instructions for an apparatus configured to execute computer-readable instructions for at least one of management of the agriculture site and application of a product to the agriculture site.

17. The method of claim 16, wherein the apparatus comprises a robotic apparatus comprising a delivery subsystem.

18. The method of claim 1, wherein executing the action comprises application of one or more microorganisms designed to promote crop health at the agriculture site.

19. The method of claim 1, wherein executing the action further comprises application of one or more of: a biofertilizer, a biocontrol agent, an agent for hormone production, an agent configured to promote stress adaptation, and a nutrient at the agriculture site.

20. The method of claim 1, wherein executing the action comprises implementing one or more of: a conventional management practice, an organic management practice, and a biodynamic management practice at the agriculture site.

* * * * *